(12) United States Patent
Subba-Reddy et al.

(10) Patent No.: US 9,296,719 B2
(45) Date of Patent: Mar. 29, 2016

(54) COMPOSITIONS AND METHODS FOR THE TREATMENT OF NOROVIRUS INFECTION

(75) Inventors: Ch. V. Subba-Reddy, Bloomington, IN (US); C. Cheng Kao, Bloomington, IN (US); Dave Smith, San Mateo, CA (US); Leo Beigelman, San Mateo, CA (US)

(73) Assignees: Indiana University Research and Technology Corporation, Indianapolis, IN (US); Alios Biopharma, Inc., South San Francisco, CA (US)

( * ) Notice: Subject to any disclaimer, the term of this patent is extended or adjusted under 35 U.S.C. 154(b) by 78 days.

(21) Appl. No.: 14/130,790

(22) PCT Filed: Jul. 9, 2012

(86) PCT No.: PCT/US2012/045911
§ 371 (c)(1),
(2), (4) Date: May 5, 2014

(87) PCT Pub. No.: WO2013/009678
PCT Pub. Date: Jan. 17, 2013

(65) Prior Publication Data
US 2014/0235683 A1    Aug. 21, 2014

Related U.S. Application Data

(60) Provisional application No. 61/505,808, filed on Jul. 8, 2011.

(51) Int. Cl.
| | | |
|---|---|---|
| *A61K 31/381* | (2006.01) |
| *A61K 31/343* | (2006.01) |
| *A61K 31/403* | (2006.01) |
| *A61P 31/14* | (2006.01) |
| *C07D 333/38* | (2006.01) |
| *C07D 307/68* | (2006.01) |
| *C07D 409/04* | (2006.01) |
| *A61K 31/5365* | (2006.01) |
| *G01N 33/50* | (2006.01) |
| *C12Q 1/66* | (2006.01) |

(52) U.S. Cl.
CPC ............ *C07D 333/38* (2013.01); *A61K 31/381* (2013.01); *A61K 31/5365* (2013.01); *C07D 307/68* (2013.01); *C07D 409/04* (2013.01); *C12Q 1/66* (2013.01); *G01N 33/502* (2013.01); *G01N 2333/91255* (2013.01); *G01N 2500/02* (2013.01); *G01N 2500/10* (2013.01)

(58) Field of Classification Search
CPC ............ A61K 31/381; A61K 31/5365; C07D 307/68; C07D 333/38; C07D 409/04; C12Q 1/66; G01N 2333/91255; G01N 2500/02; G01N 2500/10; G01N 33/502
See application file for complete search history.

(56) References Cited

U.S. PATENT DOCUMENTS

| 8,063,084 B2 * | 11/2011 | Dales et al. .................... 514/385 |
| 8,501,746 B2 * | 8/2013 | Dales et al. .............. 514/255.05 |
| 2010/0280081 A1 * | 11/2010 | Vitt et al. ...................... 514/352 |

FOREIGN PATENT DOCUMENTS

| WO | 2011/068715 | 6/2011 |
| WO | WO2012/087769 A2 * | 6/2012 |

OTHER PUBLICATIONS

Lee, et al. "Crystal structures of murine norovirus-1 RNAdependent RNA polymerase." J. Gen. Virol. Apr. 6, 2011; 92:1607-1616.

* cited by examiner

*Primary Examiner* — Nyeemah A Grazier
*Assistant Examiner* — Amanda L Aguirre
(74) *Attorney, Agent, or Firm* — Patrick J. Hagan; Dann, Dorfman, Herrell and Skillman

(57) ABSTRACT

Compositions and methods for the treatment of norovirus infection are disclosed.

4 Claims, 7 Drawing Sheets

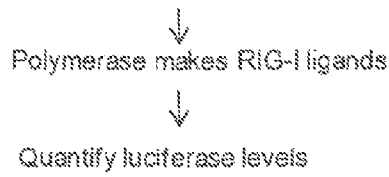
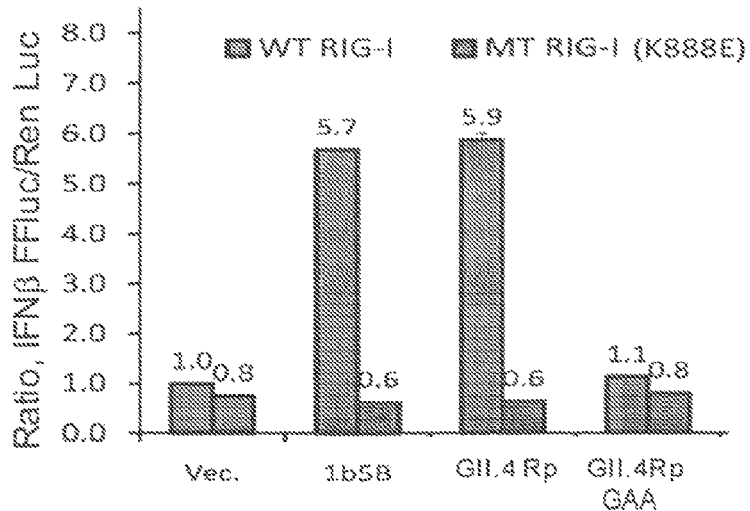
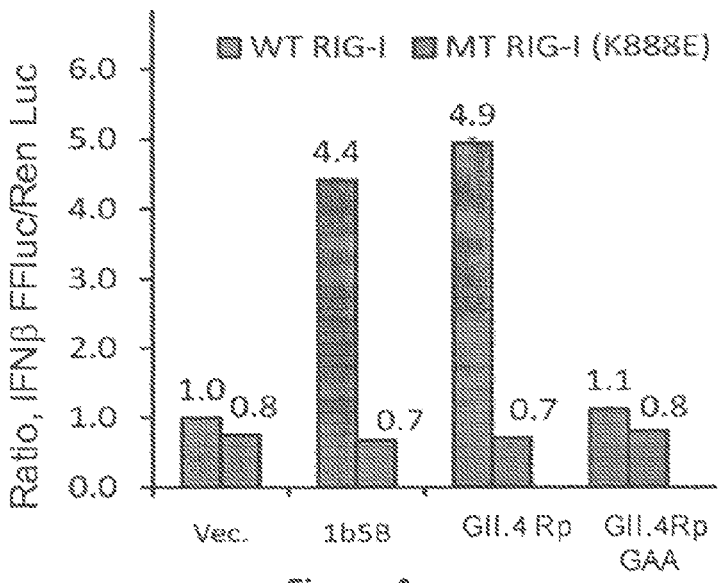
Figure 4

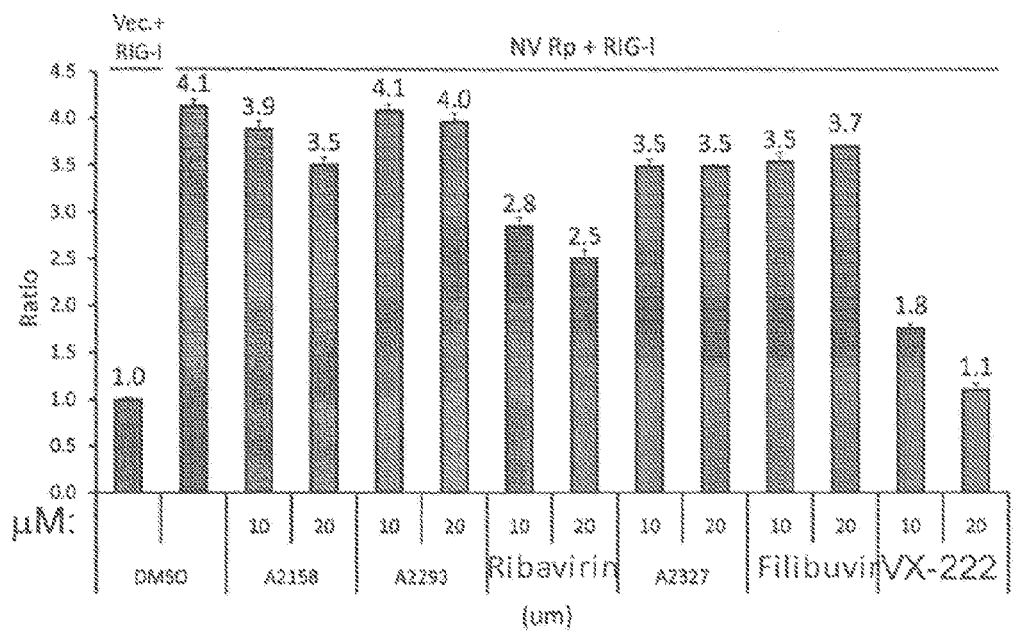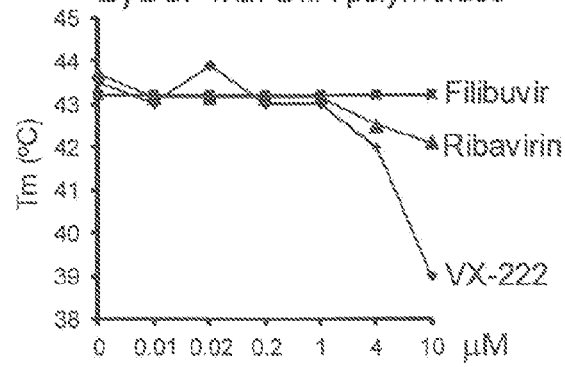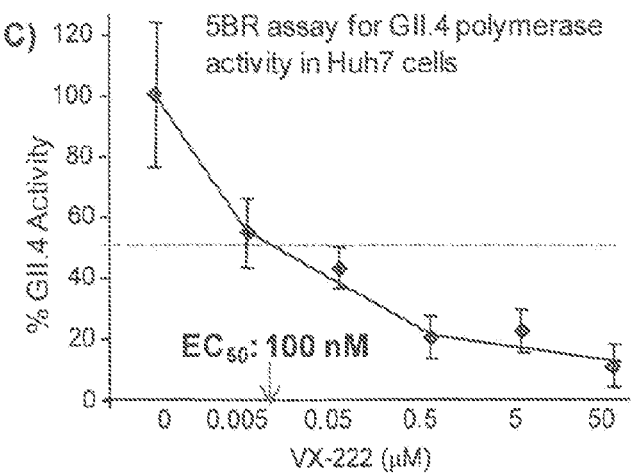
Figure 6

COMPOSITIONS AND METHODS FOR THE TREATMENT OF NOROVIRUS INFECTION

The present application is §371 application of PCT/US2012/045911 filed Jul. 9, 2012 which claims priority to U.S. Provisional Application No. 61/505,808 filed Jul. 8, 2011, the entire disclosure of each being incorporated by reference herein.

FIELD OF THE INVENTION

The present invention relates to the identification of improved anti-viral agents and methods of use thereof for treatment of viral infection, particularly norovirus infection.

BACKGROUND OF THE INVENTION

Several publications and patent documents are cited throughout the specification in order to describe the state of the art to which this invention pertains. Each of these citations is incorporated herein by reference as though set forth in full.

Noroviruses (NVs) are Category B biodefense agents and widely accepted as the major cause of viral gastroenteritis (GE). Less than 20 particles can establish a NV infection and prior exposure does not lead to protection from a repeat infection. The CDC has estimated that 64,000 hospitalizations and 900,000 clinical visits among children result from NV infection in developed countries alone (1, 2). In developing countries, NVs account for up to 200,000 deaths annually in children <5 years of age (1). Asymptomatic shedding of NVs is also a significant uncharacterized problem, with up to 12% of the UK population actively secreting virus during a study period from 1993 to 1996. At least 50% of children under age 5 are seropositive for NV exposure; this increases to 60-90% by age 10 and reaches 100% by adulthood (3). NVs are a significant cause of morbidity and mortality in immune-compromised patients, particularly those undergoing chemotherapy or stem cell transplants (4-12).

The idea that NVs cause an acute self-limiting disease with no long-lasting sequelae is under challenge. NV infections in infants can lead to seizures (13, 14) and have been linked to necrotizing enterocolitis (15). In adults NV infection can exacerbate inflammatory bowel disease (16). Increased disease severity has been linked to the use of Statins to regulate cholesterol levels in the elderly (17). Cultured cells treated with Statins show increased NV replication (18). This is especially a concern, given that 24 million Americans used Statins in 2004 and use is increasing (19).

Despite their impact on human health, NVs are one of the most poorly characterized viral groups. Studies of human NVs and the development of therapeutics are hampered by their inability to infect cells. Vaccine development is being actively pursued. However, challenges here include NVs using multiple mechanisms to persist in human populations, complex antigenic diversity and rapid virus evolution (3). Moreover, even if a vaccine should become available certain patients having genetic immune deficiencies would be unable to take such a vaccine. Clearly, a need exists in the art for improved antiviral agents which effectively and specifically inhibit norovirus replication.

SUMMARY OF THE INVENTION

In accordance with the present invention, a method for the treatment of norovirus infection associated with clinical pathology in a patient in need thereof is provided comprising administration of an effective amount of VX-222 or a pharmaceutical salt thereof to the patient, VX-222 being effective to inhibit norovirus RNA polymerase activity.

In another embodiment of the invention, new viral RNA polymerase inhibitors are provided. Exemplary compounds have the formula of formula I, wherein:
$X_1$ and $X_2$ are independently C, NH, O, or S;
$R_1$ is a lower alkyl, alkyl, cycloalkyl, or aryl;
$R_2$ is a lower alkyl, alkyl, cycloalkyl, or aryl;
$R_3$ is a lower alkyl, H, or =O;
$R_4$ is a lower alkyl, alkyl, cycloakyl, or aryl; and
$R_5$ is a lower alkyl, alkyl, cycloakyl, or aryl.

Particularly preferred inhibitors are provided in FIG. 3. Also preferred are compounds wherein $R_1$ is a carboxyl, such as a carboxylic acid, ester or amide. Also disclosed are pharmaceutical compositions comprising the inhibitors or pharmaceutically acceptable salts or prodrugs thereof in a pharmaceutically acceptable carrier.

In yet another aspect of the invention, a method for treating a viral infection in a subject in need thereof comprising administering an effective amount of at least one of the novel inhibitor compounds of the invention or a pharmaceutically acceptable salt thereof to the subject, wherein said viral infection is a norovirus infection. The method can also entail administration of other antiviral agents, such as interferon, ribavirin and the like.

The invention also provides a method for identifying agents which modulate norovirus RNA polymerase activity associated with clinical pathology. An exemplary method entails incubating cells expressing said viral RNA polymerase and at least one innate immune receptor and a reporter gene operably linked to an interferon beta promoter in the presence and absence of a test agent. Under these conditions the presence of double stranded RNA synthesized by polymerase triggers a cellular defense response which is effective to activate expression of the reporter gene. Reporter gene expression is then measured in the presence and absence of the agent, alterations of reporter gene expression in the presence of the agent being indicative of RNA polymerase modulatory activity. In another embodiment of this method, the cells are engineered to also express VPg, to facilitate characterizing the effects of the agent on the polymerase-VPg complex. The method can also comprise co-expression of additional norovirus proteins to assess whether their present or absence affects inhibitor action.

BRIEF DESCRIPTION OF THE DRAWINGS

FIG. 4 demonstrates that activities of the polymerases from NV and the MNV can be monitored in the 5BR assay format. A) Schema of the assay used. B) Ratio of the firefly to *Renilla* luciferases produced by 293T cells that express the GII.4 RdRp and either a WT (blue bars) or signaling-defective RIG-I (red bars). GAA denotes an active site mutant of the GII.4 polymerase. The HCV polymerase (1b5B) was used as a positive control. C) GII.4 polymerase activity in Huh7 cells.

FIG. 6 shows that VX-222 can inhibit GII.4 NV polymerase activity. A) Results from a confirmatory screen for inhibitors of the NV polymerase in the 5BR assay format. B) Analysis of compound binding by the recombinant NV polymerase using differential scanning fluorimetry (DSF). The data plotted is the $Tm_{app}$ from titrations of 20 pmoles of polymerase with increasing concentrations of each of the three compounds. C) $EC_{50}$ of VX-222 in cultured Huh 7 cells, a liver hepatocyte cell line. The results are reproducible in two independent assays. The GII.4 polymerase was expressed in the presence of the GII4 VP1, a protein that could enhance polymerase activity (Subba Reddy et al., in press)."

DETAILED DESCRIPTION OF THE INVENTION

Figure 1:
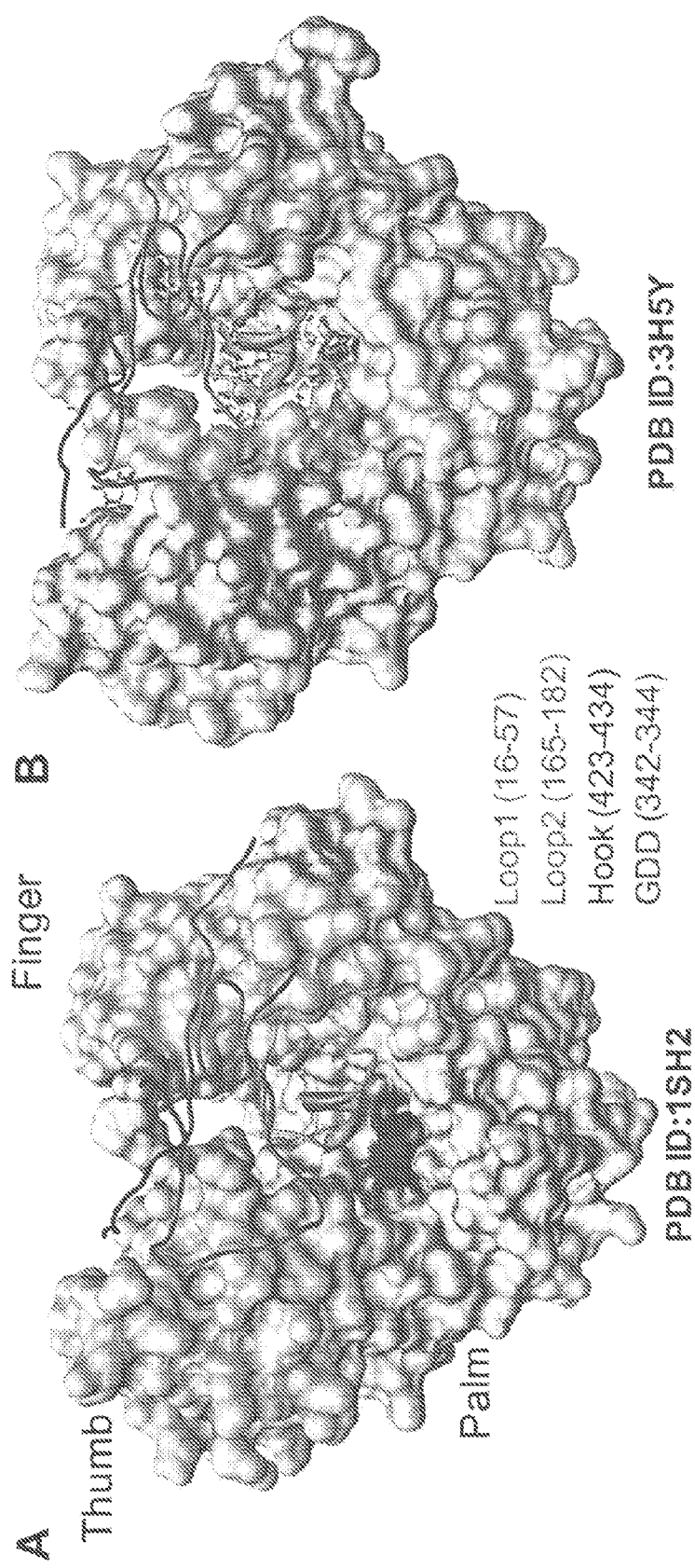
FIG. 1 shows the structure of the Norovirus (NV) polymerase. A) The apo-form of the NV polymerase. The three motifs that help to encircle the active site (colored red) are in ribbon structures. The residues for these three motifs are color-coded in the lower right corner of the panel. B) Structure of the ternary complex of the NV polymerase.

Noroviruses (family Caliciviridae) have a positive-stranded, polyadenylated RNA genome of ~7.5 kb (21). The major and minor structural proteins are encoded in ORFs 2 and 3, respectively. ORF1 encodes a ca. 200 kDa polyprotein that is proteolytically processed by the viral 3CL protease to yield six mature non-structural proteins required for proper gene expression, subgenomic transcription and genome replication. NS7, the RNA-dependent RNA polymerase (RdRp), and NS5 (VPg), the protein primer that initiates genome and subgenomic RNA synthesis (22-24) provide the therapeutic targets of the present invention.

A full cell culture system for human NV infection does not exist despite substantial efforts (25). However, several aspects of NV replication can be studied in cell cultures (24, 26, 27). Cells harboring the Norovirus replicon are available through selection of antibiotic resistance gene expressed in place of VP1 (27, 28). This replicon has been used to characterize the effect of Ribavirin, interferon, and Statins on Norovirus replication (28).

VX-222, a non-nucleoside inhibitor of the HCV polymerase developed by Vertex Pharmaceuticals is currently in Phase 2 clinical trial. While screening a library of compounds for inhibitors of human norovirus polymerase-VPg complex, we identified VX-222 as a potent inhibitor ($EC_{50}$ of less than 1 micromolar) suggesting that this molecule can be further derivatized to create a first-in-class drug against the human noroviruses. Accordingly, a series of derivatives have been synthesized and a variety of different assay methods are provided to assess specificity and inhibitory action of these compounds on the norovirus infectivity cycle.

In a particular embodiment, the compound of the instant invention has the following formula:

I 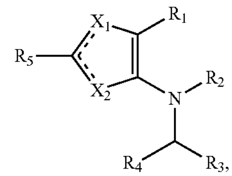 wherein:

$X_1$ and $X_2$ are independently C, NH, O, or S;

$R_1$ is a lower alkyl, alkyl, cycloalkyl, or aryl;

$R_2$ is a lower alkyl, alkyl, cycloalkyl, or aryl;

$R_3$ is a lower alkyl, H, or =O;

$R_4$ is a lower alkyl, alkyl, cycloakyl, or aryl; and $R_5$ is a lower alkyl, alkyl, cycloakyl, or aryl.

In a particular embodiment, one of $X_1$ and $X_2$ is O or S and the other is C. In a particular embodiment, $R_1$ is a carbonyl, such as a carboxylic acid, ester, amide, or aldehyde group. In a particular embodiment, $R_2$ is a cycloalkyl. In a particular embodiment, $R_3$ is H or =O. In a particular embodiment, $R_4$ is a cycloalkyl or aryl. In a particular embodiment, $R_5$ is an alkyl (particularly an alkynyl) or aryl. In yet another embodiment, $R_5$ forms an aromatic ring with either $X_1$ or $X_2$ (see, e.g., L in FIG. 3).

Definitions:

"Noroviruses" are a major cause of viral gastroenteritis, an inflammation of the linings of the stomach and small and large intestines that causes vomiting and diarrhea. Viruses are responsible for 30-40% of all cases of infectious diarrhea and viral gastroenteritis is the second most common illness in the United States, exceeded only by the common cold. Anyone can become infected with norovirus. During norovirus outbreaks there are high rates of infection among people of all ages. There are a large number of genetically-distinct strains of norovirus (29) Immunity appears to be specific for the norovirus strain and lasts for only a few months. Therefore norovirus infection can recur throughout a person's lifetime. Because of genetic (inherited) differences among humans, some people appear to be more susceptible to norovirus infection and may suffer more severe illness. People with type O blood are at the highest risk for severe infection (1). Infected individuals are contagious from the first onset of symptoms until at least three days after full recovery. Some people may remain contagious for as long as two weeks after recovery.

Noroviruses are infectious agents of humans and animals from the Caliciviridae family. Members of this family have single-stranded RNA and the virions are nonenveloped. The prototype of the human norovirus was formerly known as Norwalk virus (NV), a virus that originally gained notoriety by being associated with acute gastroenteritis in cruise ships and other closed communities of people, such as rest homes, schools, summer camps, etc. Notably, Norwalk virus, especially from genogroup GII.4, is associated with a number of pandemic outbreaks.

An "acute" viral infection is characterized by rapid onset of disease, a relatively brief period of symptoms, and resolution within days. It is usually accompanied by early production of infectious virions and elimination of infection by the host immune system. Acute viral infections are typically observed with pathogens such as influenza virus and rhinovirus.

"Persistent" infections are characterized as those in which the virus is not cleared but remains in specific cells of infected individuals. Persistent infections may involve stages of both silent and productive infection without rapidly killing or even producing excessive damage of the host cells. There are three types of overlapping persistent virus-host interaction that may be defined as latent, chronic and slow infection.

The phrase "associated with clinical pathology" when referring to a particular norovirus polymerase target refers to polymerases isolated from those strains of virus associated with both acute and chronic infection, strains isolated from immuno-compromised patients and those strains associated with gastroenteritis.

An RNA polymerase is a polymerase that catalyzes the synthesis of a complementary strand of RNA from a template nucleic acid. The template in the case of Norovirus is an RNA. Since RNA-dependent RNA polymerases are absent from human cells, these viral enzymes provide ideal therapeutic targets for the treatment of viral infection.

The term "vector" relates to a single or double-stranded circular nucleic acid molecule that can be transfected or transformed into cells and replicate independently or within the host cell genome. A circular double-stranded DNA molecule can be cut and thereby linearized upon treatment with restriction enzymes. An assortment of vectors, restriction enzymes, and the knowledge of the nucleotide sequences that are targeted by restriction enzymes are readily available to those skilled in the art. A vector of the invention includes any replicon, such as a plasmid, cosmid, bacmid, phage or virus, to which another genetic sequence or element (either DNA or RNA) may be attached so as to bring about the amplification and/or replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into RNA. In one embodiment, the promoter element of the present invention precedes the 5' end of the Norovirus nucleic acid that encodes for the viral polymerase such that the latter is transcribed into RNA. Host cell machinery then translates the RNA into polypeptides.

An "expression element" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter", "reporter system", "reporter gene", or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, polyadenylation signals, RNA splicing signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g., enhancers) in an expression vector.

The term "tag", "tag sequence", or "protein tag" refers to a chemical moiety, either a nucleotide, oligonucleotide, polynucleotide,an amino acid, peptide, protein or other chemical, that when added to another sequence, provides additional utility or confers useful properties, particularly in the detection or isolation, of that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e. g. 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e. g., flag epitope, c-myc epitope, transmembrane epitope of the influenza A virus hemagglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography.

Chemical tag moieties include such molecules as biotin, which may be added to either nucleic acids or proteins and facilitates isolation or detection by interaction with avidin reagents, and the like. Numerous other tag moieties are known to, and can be envisioned by the trained artisan, and are contemplated to be within the scope of this definition.

A "specific binding pair" comprises a specific binding member and a binding partner which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

An "antibody" or "antibody molecule" is any immunoglobulin, including antibodies and fragments thereof, that binds to a specific antigen. The term includes polyclonal, monoclonal, chimeric, and bispecific antibodies. Exemplary antibody fragments, capable of binding an antigen or other binding partner, are Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F (ab') 2 fragments, a bivalent fragment including two Fab fragments linked by a disulphide bridge at the hinge region. Single chain Fv fragments are also included.

With respect to antibodies, the term "immunologically specific" refers to antibodies that bind to one or more epitopes of a protein or compound of interest, but which do not substantially recognize and bind other molecules in a sample containing a mixed population of antigenic biological molecules.

The term "alkyl," as employed herein, includes straight and branched chain hydrocarbons containing 1 to about 20 carbons, particularly 1 to 10 carbons, in the normal chain. The hydrocarbon chain of the alkyl groups may be interrupted with one or more oxygen, nitrogen, or sulfur. The hydrocarbon may be saturated or unsaturated (e.g., comprise double bonds (alkenyl) or triple bonds (alkynyl)). Examples of suitable alkyl groups include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, the various branched chain isomers thereof, and the like. Each alkyl group may, optionally, be substituted, preferably with 1 to 4 substituents. The term "lower alkyl" refers to an alkyl which contains 1 to 3 carbons in the hydrocarbon chain. Alkyl substituents include, without limitation, alkyl, alkenyl, halo (such as F, Cl, Br, I), haloalkyl (e.g., $CCl_3$ or $CF_3$), alkoxyl, alkylthio, hydroxy, methoxy, carboxyl, oxo, epoxy, alkyloxycarbonyl, alkylcarbonyloxy, amino, carbamoyl (e.g., $NH_2C$(=O)— or NHRC(=O)—, wherein R is an alkyl), urea (—$NHCONH_2$), alkylurea, aryl, ether, ester, thioester, nitrile, nitro, amide, carbonyl, carboxylate and thiol.

The term "cyclic alkyl" or "cycloalkyl," as employed herein, includes cyclic hydrocarbon groups containing 1 to 3 rings which may be fused or unfused. Cycloalkyl groups may contain a total of 3 to 20 carbons forming the ring(s), particularly 6 or 10 carbons forming the ring(s). The cycloalkyl groups may also contain one or more rings that include at least one, particularly from 1 to about 4, sulfur, oxygen, or nitrogen heteroatom ring members. Each ring of the cycloalkyl group may be substituted, particularly with 1 to about 4 substituents, as described above for alkyls.

The term "aryl," as employed herein, refers to monocyclic and bicyclic aromatic groups containing 6 to 10 carbons in the ring portion. Examples of aryl groups include, without limitation, phenyl, naphthyl, such as 1-naphthyl and 2-naphthyl, indolyl, and pyridyl, such as 3-pyridyl and 4-pyridyl. Aryl groups may be optionally substituted through available atoms, particularly with 1 to about 4 groups. Exemplary substituents are described above. The aromatic groups may be a heteroaryl. "Heteroaryl" (encompassed by the term aryl) refers to an aromatic ring system that includes at least one, particularly from 1 to about 4, sulfur, oxygen, or nitrogen heteroatom ring members.

The terms "halogen," "halo," and "halide" particularly refer to chlorine, bromine, fluorine, or iodine.

Pharmaceuticals and Anti-Viral Therapies

The elucidation of the inhibitory action of VX-222 on norovirus RNA polymerase action described herein facilitates the development of pharmaceutical compositions useful for treatment of norovirus infection. FIG. 3 provides a series of VX-222 derivatives useful for this purpose. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. Moreover, more than one derivative may be administered in combination with one or more conventional anti-viral agents. Such agents include, without limitation, ribavirin, interferon, modified interferon, nucleoside analogs, nucleotide prodrugs, or any therapeutic combination thereof The following materials and methods are provided to facilitate the practice of the present invention.

Plasmid Constructs and Cell Cultures

NV polymerase and VPg cDNAs (Human Norovirus, GII.4, GenBank accession DQ658413) were custom synthesized based on the sequence reported for the GII.4 virus that is available in the National Center for Biotechnology Information. The cDNAs were synthesized by a commercial vendor (Origene, USA), and subcloned into pUNO vector (Invivogen Inc.) between AgeI and NheI restriction enzyme sites. N-terminal FLAG tagged NV RdRp and C-terminal FLAG- and hemagglutinin (HA)-tagged NV VPg were constructed using PCR. MNV RdRp and VPg cDNAs were PCR amplified from pET26Ub-MNV Rp and pET26Ub-MNV VPg plasmids and cloned into pUNO vector between AgeI and NheI sites. Site-directed mutagenesis used specific oligonucleotides and QuikChange site-directed mutagenesis kit (Stratagene, La Jolla, Calif.). The plasmids containing cDNAs of RIG-I (pUNO-hRIG) and MDA5 (pUNO-hMDA5) were purchased from Invivogen (San Diego, Calif.). The TLR3 plasmid (pcDNA-TLR3) was previously described in Sun et al. (30). IFNβ-Luc plasmid containing firefly luciferase reporter gene driven by a basic promoter element (TATA box) plus 5'-flanking region of the IFN-beta promoter gene, was used as reporter plasmid. pRL-TK, expressing *Renilla reniformis* luciferase driven by the Herpes Simplex virus thymidine kinase promoter, was used to monitor and standardize the efficacy of transfection (Promega, Madison, Wis., USA).

Human embryonic kidney (HEK293T) cells were cultured in DMEM GlutaMax high glucose medium (Gibco, USA) containing 10% fetal bovine serum (FBS) at 37° C. with 5% $CO_2$. The human hepatocyte cell line, Huh 7, was cultured in DMEM GlutaMax low glucose medium (Gibco, USA) supplemented with 10% FBS and lx nonessential amino acids (Gibco, USA). The murine macrophage cell line, RAW264.7, was cultured in DMEM supplemented with 10% FBS, penicillin (100 Uml) and streptomycin (100 mg/ml).

Protein Expression Analysis

Cells were harvested by gentle scrapping in 1× SDS lysis buffer and analyzed on a 4-12% NuPAGE® Novex Bis-Tris Gel and MOP S-SDS running buffer (Invitrogen, Carlsbad, Calif.). Proteins resolved in acrylamide gels were transferred to PVDF membranes (Invitrogen), membranes were blocked with 5% nonfat milk in TBS-T (Tris-buffered saline Tween-20) for 2 h and incubated overnight in blocking buffer supplemented with respective primary antibody. Following washes in TBS-T, incubated in blocking buffer supplemented with HRP conjugated secondary antibody and developed using ECL Plus™ Western Blotting Detection system (Amersham, UK). NV RdRp and VPg were detected by mouse monoclonal anti-FLAG monoclonal antibody (Sigma, USA). RNAseL was detected with anti-RNase L mouse monoclonal antibody (Millipore, USA) and β-actin with anti-βactin mouse monoclonal antibody (Santa Cruz Biotechnology, Santa Cruz, Calif.).

Differential Scanning Fluorimetry (DSF)

This method is used to examine the binding of proteins to drugs (31). The principle for the assay is that the thermal denaturation profile of the protein could be changed when it is complexed to the drug. To perform the assay, thermal melting curves of NV RdRp in the presence of inhibitors were obtained in 96-well plates using Stratagene Mx3005P Q-PCR system (Agilent Tachnologies, USA) and the fluorescent dye SYPRO Orange (Invitrogen, Carlsbad, Calif.). To evaluate the binding affinities of inhibitors, different concentrations of various drugs like VX-222, Filibuvir and Ribavirin were mixed with 20 µM purified NV RdRp and 5× concentration of SYPRO Orange. A heating rate of 1.0° C. per min was used from 25 to 90° C., and fluorescence intensity was read at excitation and emission wavelengths of 470 and 550 nm, respectively. Each sample was tested in triplicate, and the results were duplicated in at least two independent assays.

5BR Reporter Assays

The 5BR reporter assay to measure the activity of the Norovirus polymerase and other viral polymerases was performed as per Ranjith-Kumar et al. (32). The assay could also be performed with other viral proteins, such as VPg or VP1. Briefly, plasmids expressing RdRp and VPg were co-transfected along with plasmids to express RIG-I or MDA5, as well as the firefly and Renilla luciferase reporters. HEK293T or Huh 7 cells were transfected using Lipofectamine 2000 (Invitrogen, Carlsbad, Calif.) according to the manufacturer's instructions. 24 h prior to transfection, $0.75 \times 10^5$ cells were seeded into each well of Costar 96-well plates in DMEM containing 10% FBS. Cells were then typically transfected at 75% confluency with plasmid amounts detailed in the figure legends and complexed with Lipofectamine 2000 as per the manufacturer's instructions (Invitrogen, USA). Vector plasmid (pUNO-MCS) was used to maintain a constant total plasmid DNA per well. To examine the VPg effect on NV RdRp-RIG-I signaling, 293T cells were co-transfected with plasmids expressing RdRp and VPg. At 36 h after transfection, luciferase activity was measured using Dual-Glo Luciferase Assay System (Promega, Madison, Wis.) in Synergy 2 microplate reader (BioTek, Winooski, Vt.).

When used, exogenous RIG-I agonist was a 60 nucleotide hairpin triphosphorylated RNA, shR9 transfected at a 10 nM final concentration into cells using Lipofectamine 2000. TLR3 assay was performed as described by Ranjith-Kumar et al. (33), using ISRE-Luc as the firefly reporter plasmid. TLR3 expressing cells were induced with poly(I:C) (500 ng/ml; Amersham Biosciences).

A Renilla luciferase activity assay can be used to quantify the MNV replicon in the presence and absence of various inhibitors (20). $0.5 \times 10^5$ RAW264.7 cells can be seeded into each well of Costar 96-well plate. The cells at 80% confluency can be transfected with the appropriate amount of in vitro transcripts using lipofectamine 2000 as a vehicle according to the manufacturer's instructions (Invitrogen, Carlsbad, Calif.). The in vitro transcripts that did not express luciferase were transfected as background control. At 36 h after transfection, the cells are washed once with 1× PBS and the cells lysed in 20 µl of 1× passive lysis buffer. The luciferase activity can be measured using the Renilla luciferase assay system (Promega, Madison, Wis.).

Where inhibitors were added to the cells for the 5BR assay, they were added 2 h after transfection of the plasmids.

The following examples are provided to illustrate certain embodiments of the invention. They are not intended to limit the invention in any way.

EXAMPLE I

Synthesis of VX-222 Derivatives for the Treatment of Norovirus Infection

Recent evidence suggests pandemic isolates of NV are altered in their polymerase activity and this may contribute to pathogenesis (34). Accordingly inhibitors of this enzyme are highly desirable and should prove efficacious for the treatment of norovirus infection.

Similar to the structure of the HCV polymerase (35-37), the NV apoenzyme resembles that of a right hand, with the thumb, fingers, and palm subdomains (38, 39) (FIG. 1). In the HCV polymerase, a loop extends from the fingers subdomain to contact the thumb primarily though hydrophobic interactions. By encircling the template channel and rendering it spatially compatible, this loop facilitates the binding of single-stranded RNA. After the initiation of nascent RNA synthesis, steric constraints of the HCV polymerase ternary complex cause the loop to release from the thumb subdomain as the polymerase transitions to elongative RNA synthesis (40, 41). The NV has a comparable loop, which we will name Loop1 (colored magenta in FIG. 1, also see FIG. 2). A feature of the NV polymerase absent in the HCV polymerase is a hook-like structure that holds Loop1 in place (blue, FIG. 1). In the ternary structure, the distance between Loop1 and the closest residue in the thumb is increased by 4 Å when compared to the contacts in the apoenzyme (38,39). We surmise that the closed structure of the apoenzyme will change significantly upon interaction with VPg and that Loop1 and the Hook will be involved.

Figure 2:
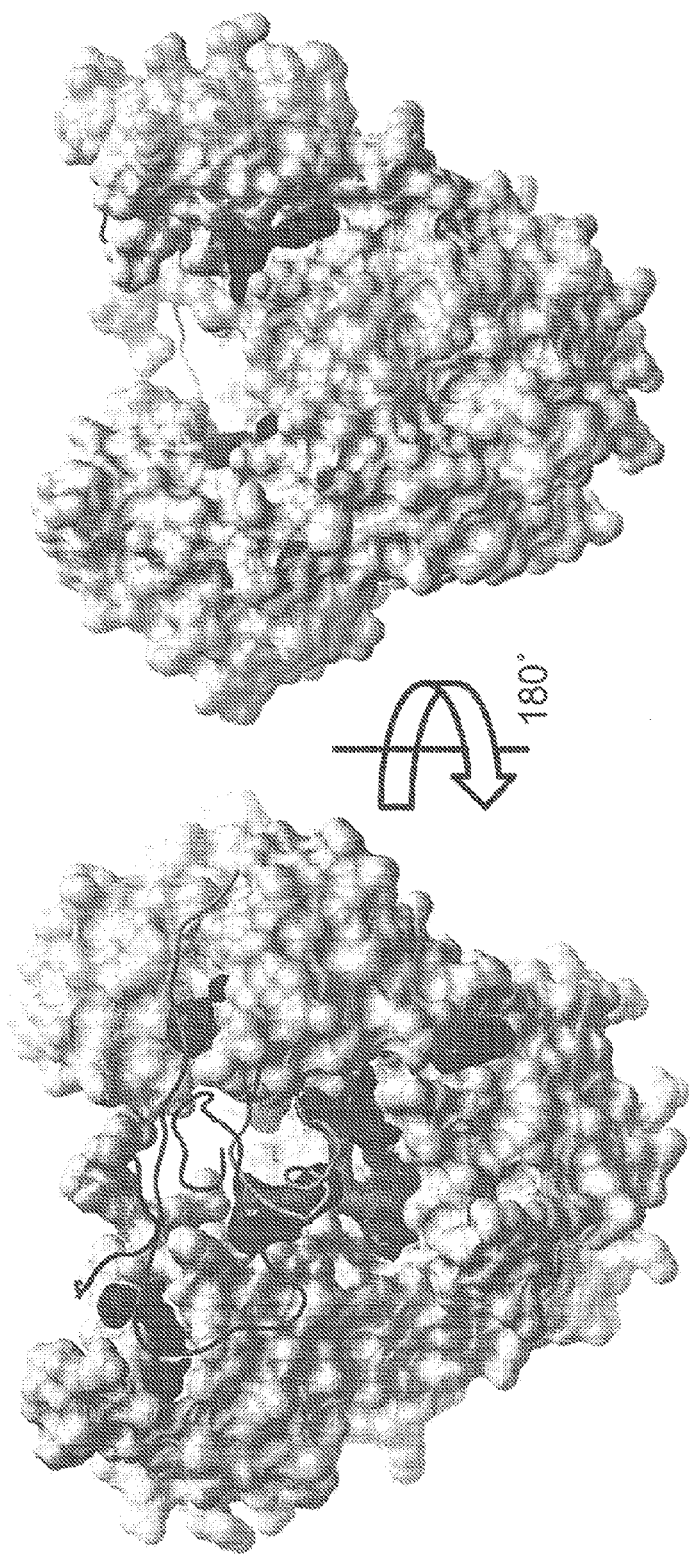
FIG. 2 shows the structure of the NV polymerase and pockets therein could be potential sites for inhibitor binding. All seven pockets have a volume in excess of 125 Å$^3$ The active site is in red.

In efforts to uncover novel features in the polymerase that could contribute to persistent infection, we will mutate pockets in the polymerase that could be sites for drug binding to facilitate an effort to develop inhibitors or the NV polymerase. The HCV polymerase has five pockets that can bind a number of inhibitors (42-44). Our initial modeling studies have identified seven pockets distinct from the active site with volumes in excess of 125 Å$^3$ (FIG. 2). We hypothesize that effective norovirus polymerase inhibitors can bind at least one of these pockets. For each, we will initially make a two-residue substitution in residues for the seven pockets shown in Table 1 and then examine whether polymerase activity will be affected in the 5BR assay in the absence and presence of co-expressed VPg. Additional mutations will be made as needed, as will biochemical examination for RNA synthesis. Pockets that cannot tolerate mutations and retain wild-type RNA synthesis should provide improved targets for rational design of inhibitors.

TABLE 1

Residues within the seven potential drug-binding pockets of the Norwalk virus polymerase designated for mutational analysis. For each of the seven pockets, two pairs of two mutations will be substituted with alanines.

| Proposed residues to mutate: | Set 1 | Set 2 |
|---|---|---|
| Pocket 1 | K166, E168 | R413, Q414 |
| Pocket 2 | Y243, R245 | S442, L443 |
| Pocket 3 | R182, L184 | S306, N309 |
| Pocket 4 | S112, D114 | M203, K207 |
| Pocket 5 | N220, N222 | R486, S488 |
| Pocket 6 | P69, E72 | G366, K368 |
| Pocket 7 | M430, P432 | R436, E465 |

VX-222 is an orally available HCV polymerase inhibitor being developed by Vertex Pharmaceuticals for use in concert with other HCV therapeutics (45). Interim results from Phase 2 clinical trial (ZENITH) had been reported and they show that VX-222 desirable pharmacokinetic, efficacy and safety profiles as well potent efficacy (46). We hypothesized that building on the VX-222 scaffold will significantly advance the drug development efforts for human NVs.

We determined that VX-222 could bind the NV polymerase (FIG. 6B). The apparent $T_m$ of the recombinant GII.4 polymerase was ~43.5° C. Ribavirin shifted the thermal denaturation profile starting at 1 µM, suggesting it can bind NV polymerase even in the nucleoside form. VX-222 shifted the denaturation profile of the GII.4 polymerase by more than 4.5° C. Filibuvir, which did not affect the 5BR assay readout, had no effect in the DSF assay. These results show that VX-222 can bind to the GII.4 polymerase in the absence of VPg. We expect that with VPg-polymerase complex, VX-222 binding will improve. We also seek to identify nucleoside inhibitors to complement the inhibitory activities of VX-222 and derivatives since a combination of inhibitors will be needed to treat any RNA virus infection.

Figure 3:
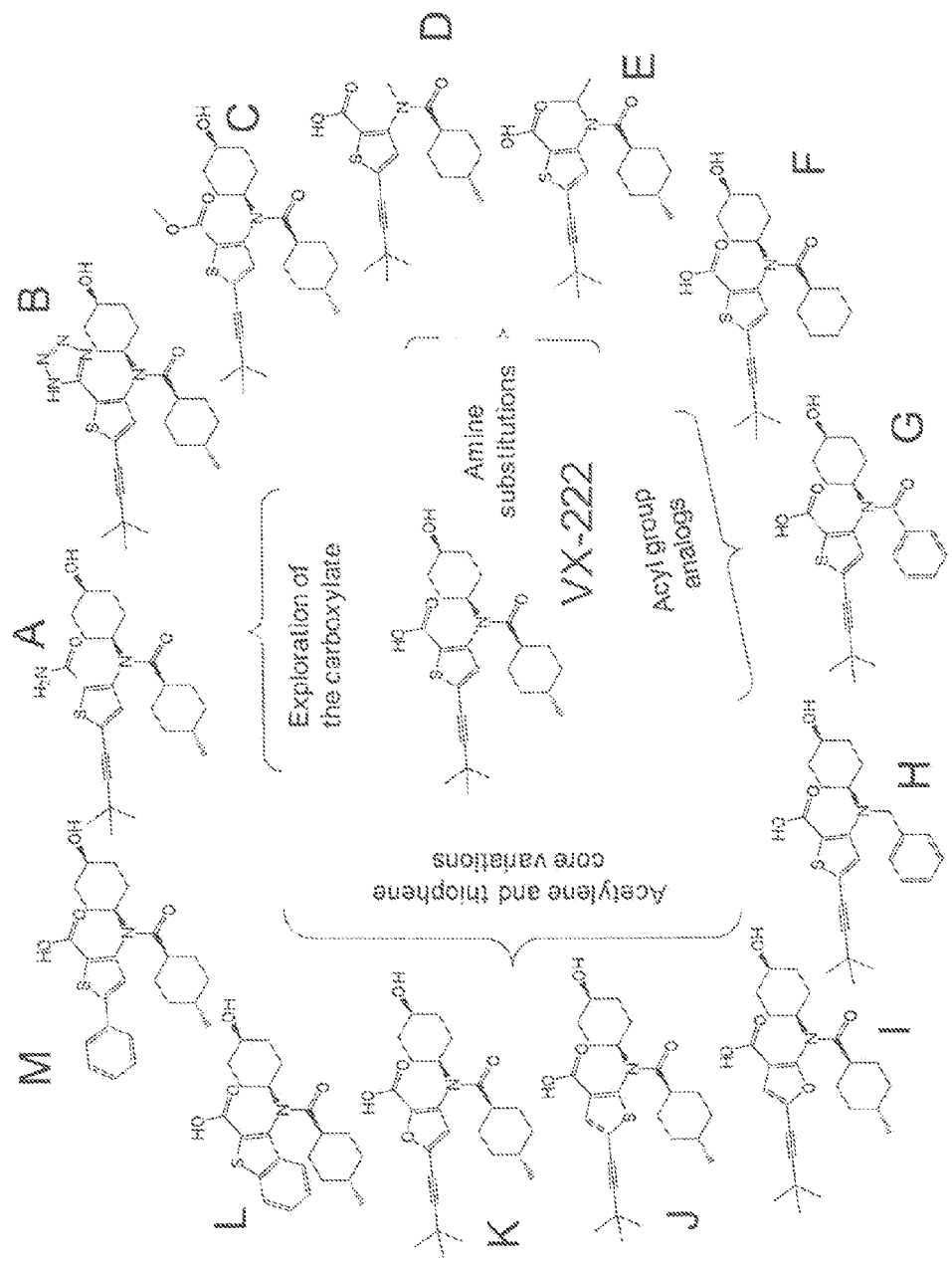
FIG. 3 shows the VX-222 derivatives of the invention.

Twelve VX-222 derivatives (named A through L) (FIG. 3) have been designed for initial testing based on preliminary structure-activity relationship (SAR) analyses. VX-222 will serve as the starting material for derivative synthesis (Scheme 1). By treatment of the carboxylic acid with an esterifying reagent, such as diazomethane or trimethylsilyldiazomethane, will be used to prepare the ester derivative C. Alternatively, Fisher esterification can be employed using refluxing methanol and a mild acid source (47). The amide derivative can be prepared from the ester via treatment with ammonia. If necessary, VX-222 can be protected and converted to the acid chloride. Reaction intermediates treated with an alcohol or ammonia could also lead to A or C. Following protection of the secondary hydroxyl of the cyclohexyl moiety, dehydration of the amide can be readily accomplished using the Burgess reagent (48, 49). The corresponding nitrile intermediate would then be reacted with trimethylsilyl azide to furnish, after silyl deprotection, the tetrazole (B). The utility of tetrazoles as bioisosteres for the carboxylic acid function has been demonstrated (50).

Other analogs proposed will be made via total synthesis. A key readily available starting material for these efforts has been described (Scheme 2; 51). The ethyl 3-aminothiophene-2-carboxylate that will serve as the starting material is commercially available. It will be converted to the trifluoroacetamide by reaction with the anhydride. The compound can then be converted to the di-lithio anion by the action of n-butyllithium, and reacted with ethylene bromide to install the halogen at the 5-position. Deprotection with potassium carbonate in ethanol furnishes the versatile bromide shown. This bromide serves as the starting material for the synthesis of VX-222 analogs in Scheme 3.

Scheme 1

Scheme 2

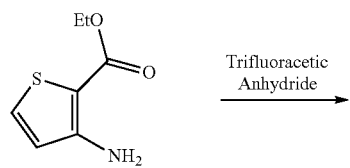

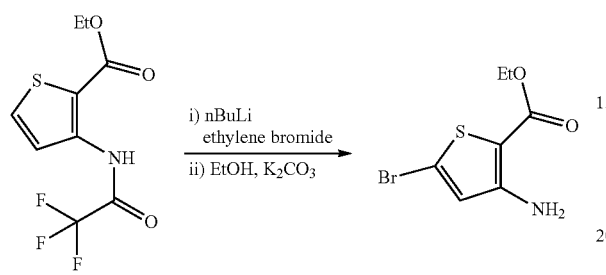

Scheme 3

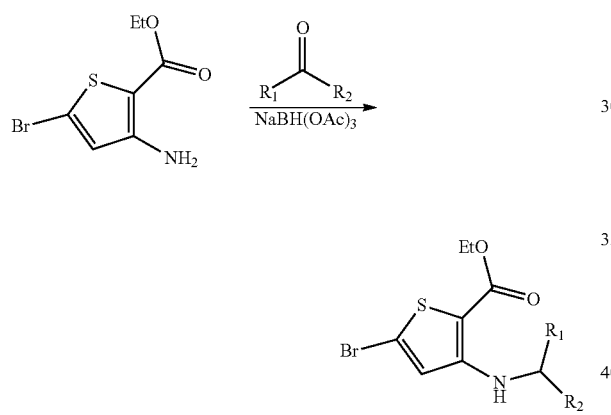

| Aldehyde/Ketone | Reductive Amination Product |
|---|---|
| 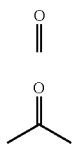 | 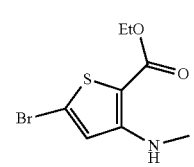 |
| 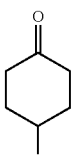 | 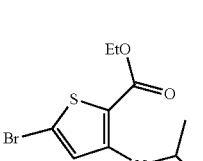 |
| 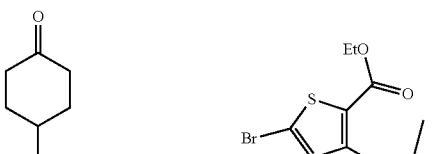 | 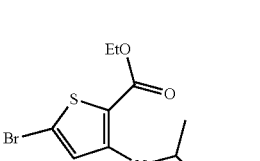 |

Reductive amination (52) engaging the 3-amino functionality with formaldehyde, acetone, or the more highly elaborated cyclohexanone would lead to intermediates that could be converted to compounds E, F, G, H and M (Schemes 4-6). In Scheme 4, synthesis of the methyl (D) and isopropyl (E) analogs is described. Coupling of the acid chloride derived from 4-methylcyclohexane carboxylate with the appropriate reductive amination product provides the amide, which would then be coupled with t-butyl acetylene in a copper (I) mediated process (53). Finally, hydrolysis of the ester to an acid would be conducted using lithium hydroxide in ethanol.

Scheme 4

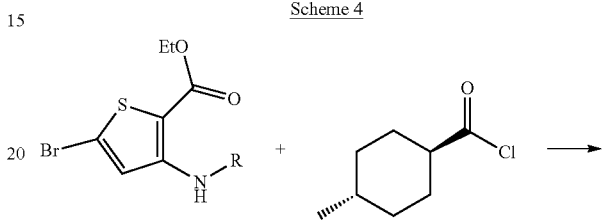

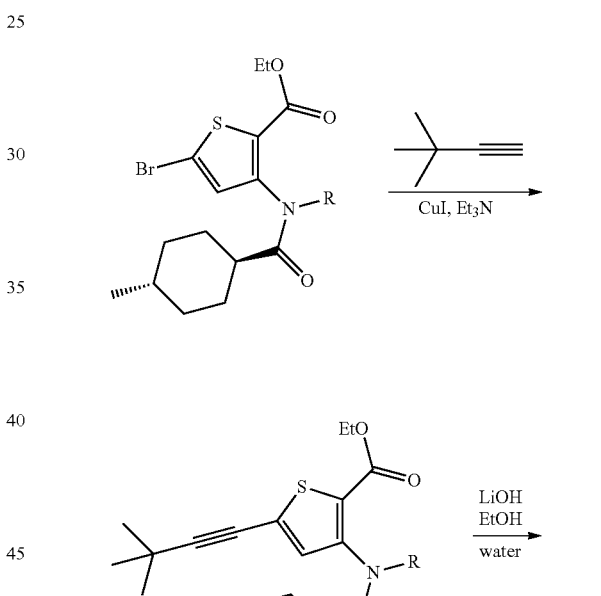

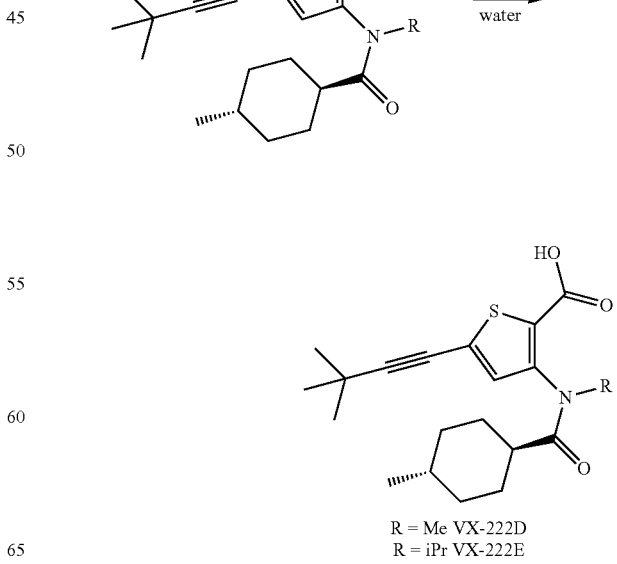

R = Me VX-222D
R = iPr VX-222E

Scheme 5
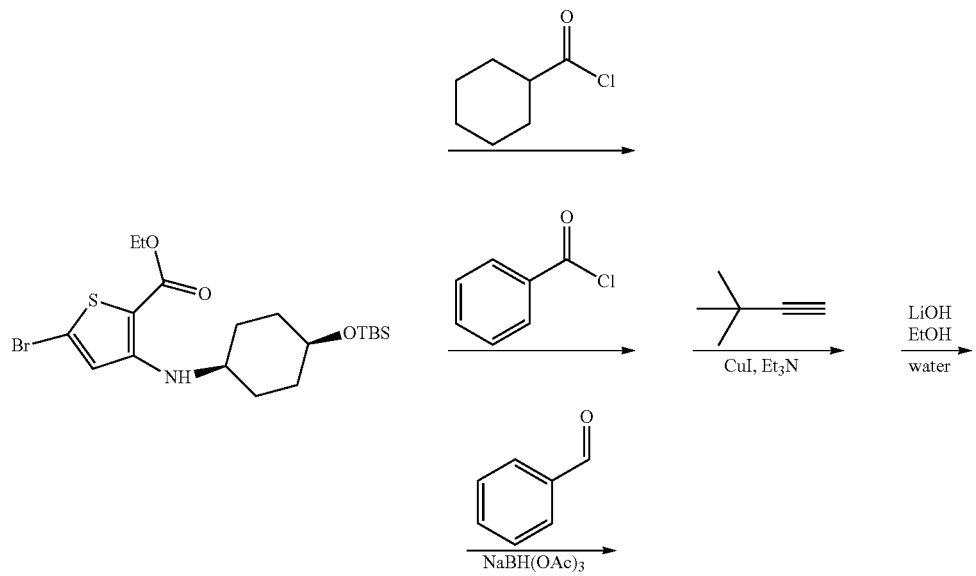
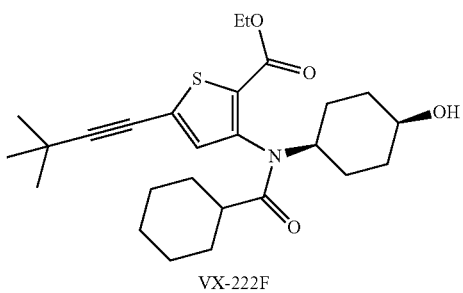
VX-222F
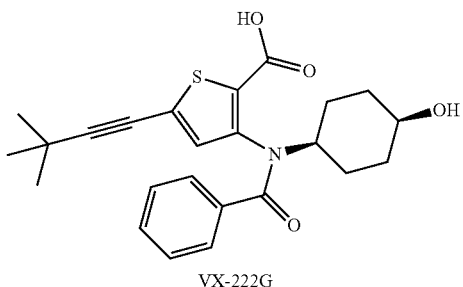
VX-222G
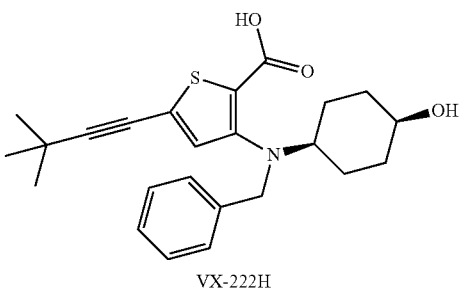
VX-222H

The more elaborate 4-hydroxy-cyclohexanone-derived amine would serve as the starting material for the analogs in Scheme 5. Through similar reaction with acid chlorides described in Scheme 4, precursors to compounds F and G would be obtained. Also the precursor (H) could be obtained by performing a second reductive amination using benzaldehyde. In each case, coupling with t-butyl acetylene would be followed by a global deprotection to afford the desired analog. If necessary, $nBu_4NF$ would be used to complete the deprotection of the silyl group. For the synthesis of analog M, in which the t-butyl acetylene will be replaced by a phenyl group, a palladium-mediated boronic acid coupling could be used to add the requisite phenyl group. Alternatively, a commercially available material is available which could lead to more straightforward synthesis of this analog (Scheme 6). Analogs I, J, K and L have phenyl replacing the acetylene along with variations of the central thiophene core of VX-222, with each requiring a distinct amino-substituted heterocycle. The requisite heterocycles can be prepared using known procedures (54,55). Synthesis of these compounds will follow the common pathway shown in scheme 7. From either of the amino heterocycles, a reductive amination using the protected 4-hydroxy-cyclohexanone would furnish the secondary amine Acylation with the acid chloride derived from 4-methylcyclohexane carboxylate would provide the amide, and a final deprotection would deliver the targeted VX-222 analogs. All compounds will be purified and their structures verified by spectroscopic techniques prior to use.

-continued

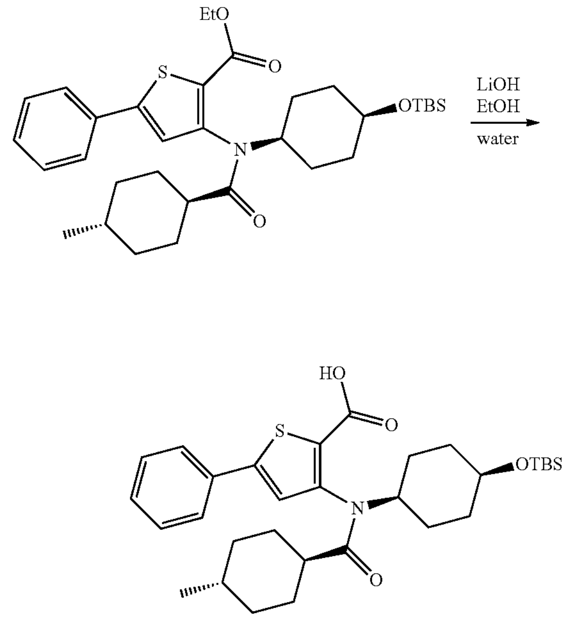

VX-222M

Scheme 6 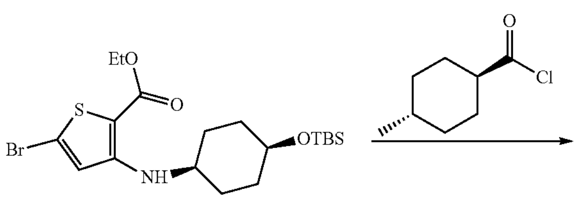 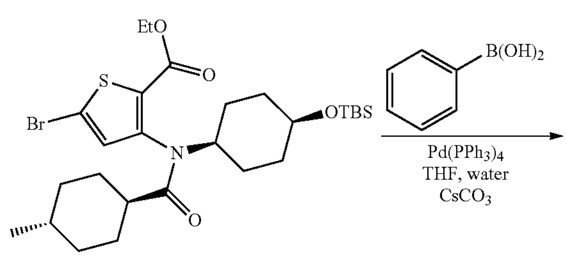 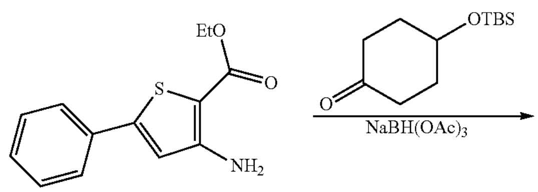 commercially available

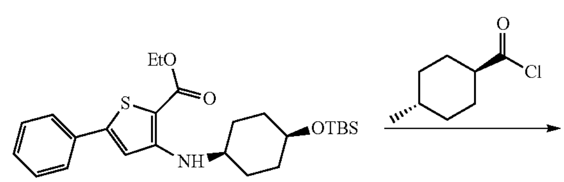

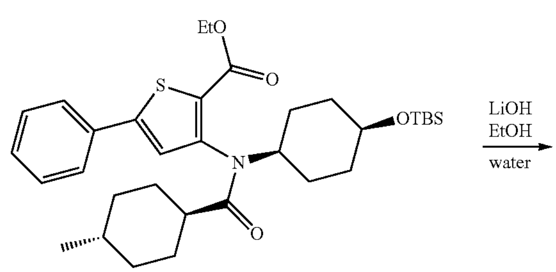

VX-222M

Scheme 7
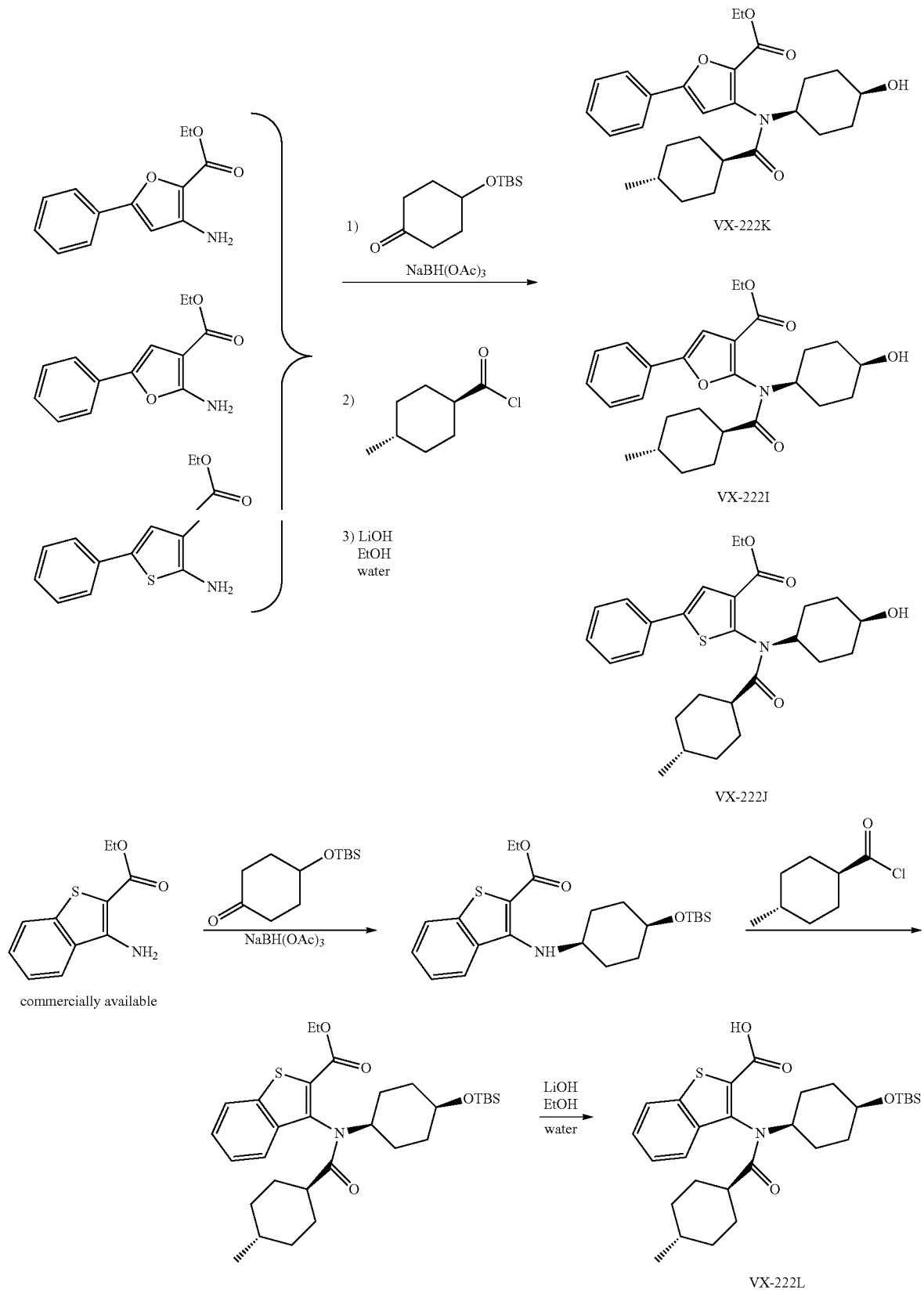

While the above schemes details the synthesis of a dozen compounds, the chemistry described is modular and could be adapted to synthesize follow-up compounds. The end-point goal is to identify a lead compound with a low nanomolar $EC_{50}$ and improved binding to the GII.4 polymerase. As mentioned above, in parallel the design of chemical inhibitors, the VX-222 binding pocket will be mapped thus enabling modeling results to inform the mode of action of these inhibitors and thereby guiding the chemistry efforts aimed towards additional potent and drug-like analogs.

EXAMPLE II

Biological and Biochemical Characterization of VX-222 Derivatives

The outcome of any viral infection depends upon the interplay between viral processes and the host innate immune responses. Viral RNAs are detected by innate immune receptors which in turn activate a suite of cellular defense responses (56-58). RIG-I and MDA5 are cytoplasmic receptors that recognize viral transcripts and replication intermediates. RNA binding by these receptors induces a conformational change to activate signaling through adaptor proteins (59-62), leading to the production of anti-viral effectors within the infected cell as well as communication between cells.

We have previously developed an easily manipulative, cell-based assay to assess RNA synthesis by viral polymerases. The 5BR assay was validated for the 1b HCV polymerase (NS5B) and has since been established for several other viruses that cannot infect cultured human cells (32 and data not shown). The assay works by having the viral polymerase synthesize RNAs, which then act as agonists to activate RIG-I and/or MDA5. Receptor activation induces Firefly luciferase reporter expression which is driven by the interferon beta promoter (FIG. 2A). A *Renilla* luciferase is expressed in the same cells to report on the transfection efficiency and possible cytopathic effects. The polymerase from the GII.4 strain of Norwalk virus is the prototype in our assay. The GII.4 NV polymerase typically yielded up to eight-fold increase in the ratio of the Firefly to the *Renilla* luciferase (FIG. 4B. An active-site polymerase mutant or a mutation in the RIG-I ligand-binding domain abolished activity in the assay, demonstrating that the assay requires RNA synthesis by the polymerase and perception of the agonist by RIG-I (FIG. 4B). Comparable results were also observed in transiently-transfected human embryonic kidney cells (293T) or hepatocytes (Huh 7) (FIGS. 4B and 4C). The same assay also works well with the Mouse norovirus polymerase, allowing mix-and-match experiments to examine specificity for viral factors and inhibitors.

Figure 5:
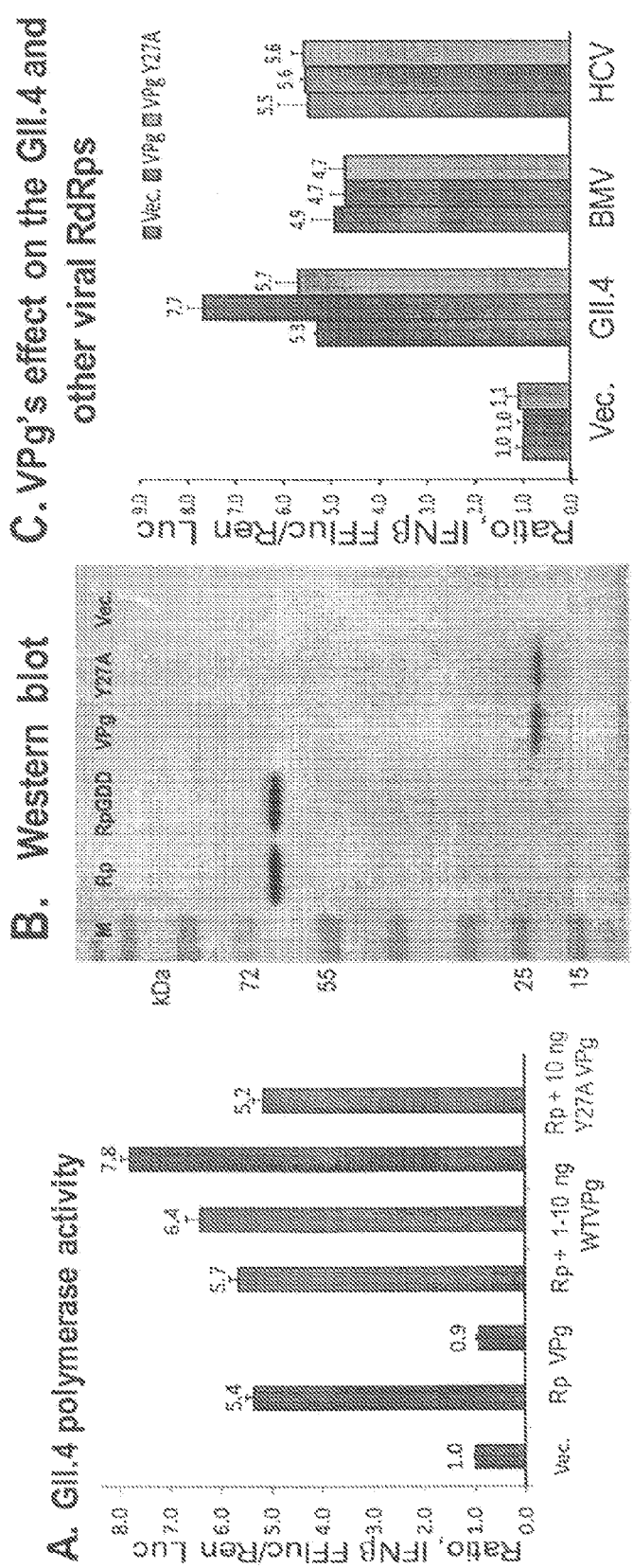
FIG. 5 shows that GII.4 polymerase activity is enhanced by the GII.4 VPg. A) Results from 293T cells co-expressing the GII.4 polymerase and increasing concentrations of the WT VPg or the uridylylation-defective Y27A mutant. B) Western blot of the proteins expressed in this experiment. C) The GII.4 VPg does not enhance activities of polymerases from brome mosaic virus and HCV.

NV polymerases can initiate by a de novo mechanism in biochemical assays performed without VPg (23). However, during viral infection, VPg is required to prime NV replication and transcription. Tyrosine residue 27 of the Norovirus VPg had been proposed to be the site for nucleotide addition (63). To reconstitute polymerase-VPg interaction, we co-expressed the two proteins and observed that VPg enhanced reporter output by two- to three-fold above assays performed with the GII.4 polymerase alone (FIG. 5A). The stimulation was highly reproducible and depended on VPg concentration expressed in the cells (FIG. 5A). A Tyr27 to alanine substitution abolished the stimulation. Furthermore, the GII.4 VPg did not stimulate the polymerases from two unrelated viruses, HCV and brome mosaic virus, demonstrating specific interaction between VPg and the GII.4 NV polymerase (FIG. 5C).

The MNV VPg stimulated the activity of the MNV polymerase (data not shown). Tyr26 of MNV VPg is the most likely site for nucleotidylation, however Tyr117 has been reported to prime RNA synthesis in biochemical assays (64). To determine whether the 5BR assay can distinguish the two putative nucleotide addition sites, we tested VPgs with alanine substitutions at residues 26 and 117 for the ability to stimulate MNV polymerase activity. Both VPg proteins were expressed at comparable levels, but only the Tyr26A substitution abolished the stimulation of the polymerase. The two mutations were also engineered into infectious MNV and only the Tyr26 substitution abolished virus production. These results show that the 5BR assay can recapitulate requirements for MNV RNA synthesis.

We seek to determine whether VPg primed RNA synthesis in the 5BR assay. The epitope-tagged VPg was immunoprecipitated from cells that co-expressed either the wild-type (WT), or an active site mutant (GAA), of the GII.4 NV polymerase. A portion of the VPg existed in a higher molecular weight form only in the presence of the WT GII4 polymerase. This result suggests that VPg serves as a protein primer in the 5BR assay. To confirm this, we selectively purified total RNA from cells expressing either the WT or inactive polymerase using silica-based resins and then probed the RNA blot to detect VPg as described previously (22). VPg was present in the RNA preparations when it was co-expressed with the WT polymerase. Treatment of an aliquot of the same samples with RNase A, not RQ1 DNase, caused VPg to shift to a lower molecular weight form. These results demonstrate that the GII.4 polymerase uses VPg as a protein primer in the 5BR assay format.

In summary, we have established a cell-based assay that faithfully duplicates requirements for NV RNA synthesis. These assays can thus be used to advantage to test the derivatives described in Example I. The VX-222 derivatives can be tested in the 5BR assay with: 1) the GII.4 polymerase, 2) the GII.4-VPg complex, 3) the MNV polymerase-VPg complex, and 4) the 1b HCV polymerase. The results will allow us to determine whether the derivatives will have improved efficacy as well as elucidate important functional groups needed for inhibition. The $EC_{50}$ values for each compound will be determined with at least seven concentrations of each compound. The 5BR assay already has an internal cytotoxicity control in the *Renilla* luciferase, but the $CC_{50}$ values for the compounds will also be determined using the WST assay that is routinely performed in the Kao lab (65). The $CC_{50}$ of the compounds as well as VX-222 will be determined in several cell lines, including 293T, Huh7, HeLa, and HT1080. All compounds will be assessed for their binding to the GII.4 polymerase using the DSF assay. Indiana University and Alios both have surface plasmon resonance (SPR) spectroscopy that will be used to determine the on- and off-rates and dissociation constants for the most promising derivatives.

The 5BR assay format has been validated for studies of nonnucleoside and nucleoside inhibitors (NNI, NI, respectively) of the 1b and 2a HCV polymerase and how resistant mutations can prevent inhibition (32). Using this format, we performed a proof-of-concept screen for inhibitor of the GII.4 polymerase. Approximately 200 compounds in our possession were tested at a single dose of 20 µM using the 5BR assay format. The hits were re-screened at 10 and 20 µM final concentrations (FIG. 6A). Ribavirin was found to have a modest inhibitory effect, with an $EC_{50}$. This is consistent with the results of Chang et al., (18) although Ribavirin is known to have pleiotropic effects on cellular as well as viral processes (66).

Using this screen, we observed that NNI VX-222, which binds to the Thumb II pocket of the HCV polymerase, inhibited the GII4 and the MNV polymerase with $EC_{50}$s of ~15 μM. Filibuvir, another Thumb II NNI of the HCV polymerase had no effect (FIG. 6A). VX-222 did not affect RIG-I signaling in the absence of the NV polymerase (data not shown). Surprisingly, when VX-222 was tested with the GII.4 polymerase-VPg complex, the observed $EC_{50}$ was lowered to 0.9 μM (FIG. 6B). To determine whether VX-222 can inhibit the GII.4 polymerase activity, we used the 5BR cell-based assay. VX-222 exhibited concentration-dependent inhibition of the GII.4 NV polymerase activity in Huh7 cells (FIG. 6C). The effective concentration for inhibition of HEK293T cells was approximately 0.1 μM. These results show that the GII.4 polymerase-VPg complex has different drug binding sites when compared to the polymerase alone.

Figure 7:
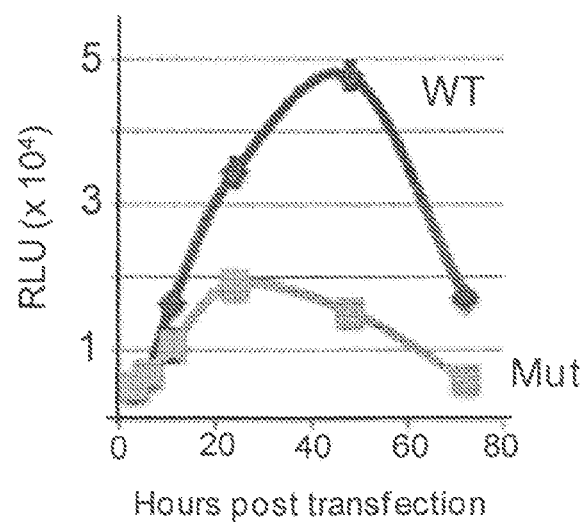
FIG. 7 shows results obtained using a real-time mouse norovirus (MNV) replicon developed in Subba Reddy et al. (20). Capped transcripts generated from either a WT or polymerase active site mutant of a clone of MNV that contains *Gaussia* luciferase was transfected into cells and the secreted luciferase monitored over time. The data contains the mean with standard deviations from three independent samples. This assay is also useful for assessing the inhibitory actions of the derivatives disclosed herein.

Finally, we will test the VX-222 derivatives in the GII.4 and MNV replicons. We have access to an MNV replicon in Huh7 cells that can express a secreted luciferase which allows for the rapid quantification of viral genome replication (FIG. 7; 20). We also have access to a Norovirus replicon in human gastric tumor cells (unpublished data). These cells form microvilli and tight junctions in culture, while they also posses the ability to secret H+ upon histamine treatment, providing the most relevant NV replicon system generated to date. The effects of the VX-222 derivatives on the replicons will be quantified by RT-qPCR and Western blot for viral proteins. Known inhibitors of NV replication, e.g. hippuristanol (targeting eIF4A) and ribavirin, will be used as controls (67).

EXAMPLE III

In Vivo Testing of the Inhibitors of the Invention

VX-222 derivatives and nucleoside analogs such as ribavirin and other antiviral agents will be tested alone and in combination in primary infected cells and whole animal systems. Growth of MNV will be examined in mouse BMDM cells treated with varying doses of the two VX-222 derivatives and two nucleoside analogs. Based on previous studies, we will require 25 WT mice and 40 from a STAT1-/-background, with the latter being expected to produce virus at a faster rate due to the lack of an effective innate immune response (68). Viral infection will be quantified by RT-qPCR at 0, 6, 12, 18 and 30 h after virus addition. Cells harvested 18 and 30 h after infection will be enumerated for plaque forming units and to detect MNV structural and nonstructural proteins.

We will also assess the effects of the derivatives described in Example I in vivo by examining the effects of inhibitors on MNV infection in mice. An initial pilot experiment will be used to determine the highest tolerated dose of the compounds in WT mice compared to control-treated mice. For example, three doses of each of the at least four inhibitors will be tested. For each dose, mice will be treated orally daily (by gavage). The effect of treatment on weight, food and water intake will be monitored using metabolic cages. Blood will be collected for enzyme and biomarkers (ALT, AST, cytochrome P450, IL6, TNF, etc.) (69-70) to provide additional information on tolerance. The organs will be collected 12 h after the final dose for weights and histopathology.

In an exemplary approach, two experimental MNV models will be tested with the inhibitors. MNV1 in an immunocompetent background will be used to model acute infections that are resolved within 5-7 days (68,71). MNV3 in immunocompetent mice will be used as a model of NV persistence as infection continues for many months (72). The latter can serve as a model for long-term secretion of NV. The efficacy results from the 5BR assays for the selected inhibitors will be confirmed prior to these in vivo experiments.

For assessing treatment of acute infection, groups of mice will be treated with a single dose of inhibitor at the highest tolerated concentration at 1 day before, during and after virus inoculation. Mice will be weighed daily and viral titers will be determined in the various organs of groups of 12 mice per treatment at days 1, 3 and 5 post infection or days 2, 4 and 6 in the case of mice treated 1 day post infection. Samples will be analyzed by plaque assay, RT-qPCR for viral genome and histology and subjected to statistical analysis.

For assessing treatment of persistent infection, groups of 12 mice will be treated with a single dose of inhibitor at the highest tolerated concentration at one of three times: 1 day before, during and after virus inoculation. The mice will be weighed daily and viral titers will be determined in the feces collected every two days and analyzed for MNV3 by RT-qPCR and plaque formation assays. For half of each cohort, various organs at will be collected at 10 days post infection and the remainder will be collected at 21 days post infection. All samples will be analyzed by plaque assay, RT-qPCR for viral genome and histology and the results subjected to statistical analysis.

The effects of the polymerase inhibitors of the invention on the prophylactic treatment of persistent NV infection can also be determined Individuals on immunosuppressive therapy or have genetic immune deficiency and some elderly individuals can experience long-term infections with NVs. To model the effect of inhibitors for these individuals, we will examine the ability of the inhibitors on MNV from persistently infected mice. Groups of 12 mice will be inoculated with MNV3 and allowed to establish persistent infection (21 days). The mice will then be treated with the highest tolerated dose of inhibitor as either a single daily does for up to 7 days, or every 2 days for 14 days, with viral secretion being monitored in the feces on a daily basis. At day 14 after the initiation of treatment (12 h after the last dose for the group receiving inhibitor for 14 days), the mice will be euthanized and organs harvested for plaque assay, RT-qPCR for viral genome and histology. The information on acute and persistent studies will provide guidance to the clinician as to the most appropriate use of the inhibitors in disease indications associated with NV infection.

REFERENCES

1. Patel M M, Hall A J, Vinje J, Parashar U D. (2009) Noroviruses: A comprehensive review. J Clin Virol 44,1-8.
2. Scallan E, Hoekstra R M, Angulo F J, Tauxe R V, Widdowson M A, et al. (2011) Foodborne illness acquired in the United States—major pathogens. Emerg Infect Dis 17,7-15.
3. Donaldson E F, Lindesmith L C, LoBue A D, Baric R S. (2010) Viral shape-shifting: norovirus evasion of the human immune system. Nature Reviews Microbiology, 8,231-241.
4. Schwartz S, Vergoulidou M, Schreier E, Loddenkemper C, Reinwald M, et al. (2011) Norovirus gastroenteritis causes severe and lethal complications after chemotherapy and hematopoietic stem cell transplantation. Blood 117,5850-5856.
5. Saif M A, Bonney D K, Bigger B, Forsythe L, Williams N, et al. (2011) Chronic norovirus infection in pediatric hematopoietic stem cell transplant recipients: A cause of 6. Roos-Weil D, Ambert-Balay K, Lanternier F, Mamzer-Bruneel M F, Nochy D, et al. (2011) Impact of Norovirus/Sapovirus-related diarrhea in renal transplant recipients hospitalized for diarrhea. Transplantation. doi: 10.1097/TP.0b013e31821c9392.
7. Capizzi T, Makari-Judson G, Steingart R, Mertens W C (2011) Chronic diarrhea associated with persistent norovirus excretion in patients with chronic lymphocytic leukemia: report of two cases. BMC Infect Dis 11,131.
8. Blanco N B, Kuonen R, Bellini C, Manuel O, Estrade C, et al. (2011) Chronic norovirus gastroenteritis in a double hematopoietic stem cell and lung transplant recipient. Transpl Infect Dis 13,213-215.
9. Schorn R, Hohne M, Meerbach A, Bossart W, Wuthrich R P, et al. (2010) Chronic norovirus infection after kidney transplantation: molecular evidence for immune-driven viral evolution. Clin Infect Dis 51: 307-314.
10. Henke-Gendo C, Harste G, Juergens-Saathoff B, Mattner F, Deppe H, et al. (2009) New Real-Time PCR Detects Prolonged Norovirus Excretion in Highly Immunosuppressed Patients and Children. J Clin Microbiol 47,2855-2862.
11. Gallimore C I, Lewis D, Taylor C, Cant A, Gennery A, et al. (2004) Chronic excretion of a norovirus in a child with cartilage hair hypoplasia (CHH). J Clin Virol 30,196-204.
12. Roddie C, Paul J P, Benjamin R, Gallimore C I, Xerry J, et al. (2009) Allogeneic hematopoietic stem cell transplantation and norovirus gastroenteritis: a previously unrecognized cause of morbidity. Clin Infect Dis 49,1061-1068.
13. Chen S Y, Tsai C N, Lai M W, Chen C Y, Lin K L, et al. (2009) Norovirus infection as a cause of diarrhea-associated benign infantile seizures. Clin Infect Dis 48,849-855.
14. Medici M C, Abelli L A, Dodi I, Dettori G, Chezzi C (2010) Norovirus RNA in the blood of a child with gastroenteritis and convulsions—A case report. J Clin Virol 48,147-149.
15. Turcios-Ruiz R M, Axelrod P, St John K, Bullitt E, Donahue J, et al. (2008) Outbreak of necrotizing enterocolitis caused by norovirus in a neonatal intensive care unit. J Pediatr 153,339-344.
16. Khan R R, Lawson A D, Minnich L L, Martin K, Nasir A, et al. (2009) Gastrointestinal norovirus infection associated with exacerbation of inflammatory bowel disease. J Pediatr Gastroenterol Nutr 48,328-333.
17. Rondy M, Koopmans M, Rotsaert C, Van Loon T, Beljaars B, et al. (2011) Norovirus disease associated with excess mortality and use of statins: a retrospective cohort study of an outbreak following a pilgrimage to Lourdes. Epidemiol Infect 139,453-463.
18. Chang K O and George D W. (2007) Interferons and ribavirin effectively inhibit Norwalk virus replication in replicon-bearing cells. J Virol 81,12111-8.
19. Mann D, Reynolds K, Smith D, Muntner P (2008) Trends in statin use and low-density lipoprotein cholesterol levels among US adults: impact of the 2001 National Cholesterol Education Program guidelines. Ann Pharmacother 42,1208-1215.
20. Subba-Reddy C V, Yunus M A, Goodfellow I G, Kao C C. 2012 Norovirus RNA synthesis is modulated by an interaction between the Viral RNA-dependent RNA polymerase and the major capsid protein, VP1. J. Virol. (In press).
21. Hardy M E. (2005) Norovirus protein structure and function. FEMS Micro Lett 253,1-8.
22. Chaudhry Y, Nayak A, Bordeleau M E, Tanaka J, Pelletier J, Belsham G J, Roberts L O, Goodfellow I G. (2006) Caliciviruses differ in their functional requirements for eIF4F components. J Biol Chem, 281: 25315-25.
23. Rohayem J, Jager K, Robel I, Scheffler U, Temme A and Rudolph W. (2006) Characterization of norovirus 3Dpol RNA-dependent RNA polymerase activity and initiation of RNA synthesis. J Gen Virol 87,2621-2630.
24. Guix S, Asanaka M et al. (2007). "Norwalk virus RNA is infectious in mammalian cells." J Virol 81,12238-12248.
25. Duizer E, Schwab K J, Neill F H, Atmar R L, Koopmans M P, et al. (2004) Laboratory efforts to cultivate noroviruses. J Gen Virol 85,79-87.
26. Asanaka M, Atmar R L et al. (2005). "Replication and packaging of Norwalk virus RNA in cultured mammalian cells." Proc Natl Acad Sci USA 102,10327-10332.
27. Chang K O, Sosnovtsev S V, Belliot G, King A D, Green K Y. (2006) Stable expression of a Norwalk virus RNA replicon in a human hepatoma cell line. Virology 353,463-473.
28. Chang K O (2009) Role of cholesterol pathways in norovirus replication. J Virol 83,8587-8595.
29. Green, K Y (2007) In D. M. Knipe, P. M. Howley, D. E. Griffin, R. A. Lamb, M. A. Martin, B. Roizman, S. E. Straus (ed), Fields Virology. 5 ed, vol. 2. Lippincott Williams & Wilkins, Philadelphia, Pa. pp. 949-980
30. Sun J, Duffy K, Ranjith-Kumar C T, Masarapu H, Lamb R, Holzenburg A, Cunningham M, Sarisky R T, Mbow M L, Kao C C. (2006) Functional and structural analyses of the human Toll-like Receptor 3. J. Biol. Chem. 281,11144-11151.
31. Niesen F H, Berglund H, Vedadi M. (2007) The use of differential scanning fluorimetry to detect ligand interactions that promote protein stability. Nat. Protoc. 2,2212-2221.
32. Ranjith-Kumar C T, Wen Y, Baxter N, Bhardwaj K, Kao C C (2011) A cell-based assay for RNA synthesis by the HCV polymerase reveals new insights on mechanism of polymerase inhibitors and modulation by MS5A. PLoS ONE. 6(7),e22575.
33. Ranjith-Kumar C T, Miller W, Santos J, Cleveland L, Park M, Duffy K E, Lamb R, Sarisky R T, Mbow L, Kao C C. (2007) Biochemical and Functional Analyses of the Human Toll-like Receptor 3 Ectodomain. J. Biol. Chem. 282,7668-7678.
34. Bull R A and White P A. (2011) Mechanisms of GII.4 norovirus evolution. Trends Microbiol 19,233-240.
35. Lesburg C A, Cable M B, Ferrari E, Hong Z, Mannarino A F, Weber P C. (1999) Crystal structure of the RNA-dependent RNA polymerase from hepatitis C virus reveals a fully encircled active site. Nat Struct Biol. 6,937-943.
36. Bressanelli S, Tomei L, Roussel A, Incitti I, Vitale R L, Mathieu M, De Francesco R, Rey F A. (1999) Crystal structure of the RNA-dependent RNA polymerase of hepatitis C virus. Proc Natl Acad Sci USA. 96,13034-13039.
37. Biswal B K, Cherney M M, Wang M, Chan L, Yannopoulos C G, Bilimoria D, Nicolas O, Bedard J, James M N. (2005) Crystal structures of the RNA-dependent RNA polymerase genotype 2a of hepatitis C virus reveal two conformations and suggest mechanisms of inhibition by non-nucleoside inhibitors. J Biol Chem. 280,18202-18210.
38. Ng K K, Pendás-Franco N, Rojo J, Boga J A, Machin A, Alonso J M, Parra F (2004) Crystal structure of Norwalk virus polymerase reveals the carboxyl terminus in the active site cleft. J Biol Chem 279,16638-16645.

39. Zamyatkin D F, Parra F, Alonso J M, Harki D A, Peterson B R, Grochulski P, Ng K K. (2008) Structural insights into mechanisms of catalysis and inhibition in Norwalk virus polymerase. J Biol Chem 283,7705-7712.
40. Chinnaswamy S, Yarbrough I, Palaninathan S, Kumar C T, Vijayaraghavan V, et al. (2008) A locking mechanism regulates RNA synthesis and host protein interaction by the hepatitis C virus polymerase. J Biol Chem 283,20535-20546.
41. Chinnaswamy S, Ayaluru M, Fujisaki K, Li P and Kao C C. (2010) Regulation of de novo initiated RNA synthesis in the hepatitis C virus RNA-dependent RNA polymerase by intermolecular interactions, J Virol 84,5923-5935.
42. Ma H, Leveque V, De Witte A, Li W, Hendricks T, Clausen S M, Cammack N, Klumpp K. (2005) Inhibition of native hepatitis C virus replicase by nucleotide and non-nucleoside inhibitors. Virology 332,8-15.
43. Carroll S S and Olsen D B. (2006) Nucleoside analog inhibitors of hepatitis C virus replication. Infect Disord Drug Targets. 6,17-29.
44. Koch U, Narjes F. (2007) Recent progress in the development of inhibitors of the hepatitis C virus RNA-dependent RNA polymerase. Curr Top Med Chem 7,1302-1329.
45. Monthly prescribing reference Article 199696. Phase 2 Study of VX-222 in Combination with Telaprevir, Pegylated-Interferon and Ribavirin for Hepatitis C. Mar. 31, 2011.
46. Jun. 9, 2011 Vertex Press release. http://investors.vrtx.com/releasedetail.cfm?ReleaseID=583683
47. Chan L, et al. (2008) Thiophene analogues for the treatment or prevention of flavivirus infections. US2008299080A1.
48. Burgess E M, Penton Jr. H R, Taylor E A. (1973) Thermal reactions of alkyl N-carbomethoxy-sulfamate esters. J Org Chem, 38,26.
49. Claremon D A, Phillips B T. (1988) An efficient chemoselective synthesis of nitriles from primary amides. Tetrahedron Letters, 29(18),2155.
50. Pinter T, Jana S, Courtemanche R J M, Hof F. (2011) Recognition properties of carboxylic acid bioisosteres: anion binding by tetrazoles, aryl sulfonamides, and acyl sulfonamides on a calix[4]arene scaffold. J Org Chem 76,3733.
51. Zhang M, Tamiya J, Nguyen L, Rowbottom M W, Dyck B, Vickers T D, Grey J, Schwarz D A, Heise C E, Haelewyn J, Mistry M S, Goodfellow V S. (2007) Thienopyrimidinone bis-aminopyrrolidine ureas as potent melanin-concentrating hormone receptor-1 (MCH-R1) antagonists. Bioorg and Med Chem Lett 17,2535.
52. Abdel-Magid A F, Maryanoff C A and Carson K G. (1990) Reductive amination of aldehydes and ketones by using sodium triacetoxyborohydride. Tetrahedron Lett 31,5595.
53. D'Auria M, Mico A D, D'Onofrio F, Piancatelli G. (1987) Synthesis of naturally occurring bithiophenes: A photochemical approach. J Org Chem 52,5243.
54. Redman A M, Dumas J, and Scott W J (2000) Preparation of 5-substituted 3-aminofuran-2-carboxylate esters. Org Lett 2,2061.
55. Foley L H. (1994) An efficient synthesis of 2-chloro-3-carboethoxy- or 2-chloro-3-cyano-4,5-disubstituted and 5-substituted pyrroles. Tetrahedron Lett 35,5989.
56. Pichlmair A, Schulz O, Tan C P, Näslund T I, Liljeström P, Weber F, Reis e Sousa C (2006) RIG-I-mediated antiviral response to single-strand RNA bearing 5'-phosphates. Science 314,997-1001.
57. Samuel C E (2001) Antiviral actions of interferons. Clin Micro Rev. 14,778-809.
58. Fensterl V, Sen G C. (2009) Interferons and viral infections. Biofactors 35,14-20.
59. Seth R B, Sun L, Ea C K, Chen Z J (2005) Identification and characterization of MAVS, a mitochondrial antiviral signaling protein that activates NF-kappaB and IRF 3. Cell 122: 669-682.
60. Foy E, Li K, Sumpter R, Jr., Loo Y M, Johnson C L, et al. (2005) Control of antiviral defenses through hepatitis C virus disruption of retinoic acid-inducible gene-I signaling. Proc Natl Acad Sci USA 102,2986-2991.
61. Xu L G, Wang Y Y, Han K J, Li L Y, Zhai Z, et al. (2005) VISA is an adapter protein required for virus-triggered IFN-beta signaling. Mol Cell 19,727-740.
62. Meylan E, Curran J, Hofmann K, Moradpour D, Binder M, et al. (2005) Cardif is an adaptor protein in the RIG-I antiviral pathway and is targeted by hepatitis C virus. Nature 437,1167-1172.
63. Belliot G, Sosnovtsev S V, Chang K O, McPhie P, Green K Y. (2008) Nucleotidylylation of the VPg protein of a human norovirus by its proteinase-polymerase precursor protein. Virology 374,33-49.
64. Han K R, Choi Y, Min B S, Jeong H, Kim J et al. (2010) Murine norovirus-1 3Dpol exhibits RNA-dependent RNA polymerase activity and nucleotidylates on Tyr of VPg. J Gen Virol 91,171301722.
65. Ranjith-Kumar C T, Lai Y Y, Sarisky R T, Kao C C (2010) Green tea catechin, epigallocatechin gallate, suppresses signaling by the dsRNA innate immune receptor RIG-I. PLoS One 5(9),e12878.
66. Graci J D, Cameron C E. (2004) Challenges for the development of ribonucleoside analogues as inducers of error catastrophe, Antiviral Chem Chemotherap 15,1-13.
67. Vashist S, Bailey D, Putics A, Goodfellow I (2009). Model systems for the study of human norovirus biology. Fut Virol. 4,353-367.
68. Karst S M, Wobus C E, Lay M, Davidson J, Virgin H W 4th (2003) STAT1-dependent innate immunity to a Norwalk-like virus. Science 7,1575-1578.
69. Guengerich F P. Cytochrome p450 and chemical toxicology. Chem. Res. Toxicol. 2008, 21,70-83.
70. Valsman N, Lebovitz E, Dagan R, and Barak V. (2003) The involvement of IL6 and IL-8 in acute invasive gastroenteritis of children. Cytokine 22,194-197.
71. Wobus C E, Karst S M, Thackray L B, Chang K O, Sosnovtsev S V, Belliot G, Krug A, Mackenzie J M, Green K Y, Virgin H W. (2004) Replication of Norovirus in cell culture reveals a tropism for dendritic cells and macrophages. PLoS Biol 2:e432.
72. Ward J M, Wobus C E, Thackray L B, Erexson C R, Faucette L J et al. (2006). Pathology of immunodeficient mice with naturally occurring norovirus infection. Toxicol Pathol 34,708-715.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable modification without departure from the scope of the appended claims.

What is claimed is:

1. A method for treating a viral infection in a subject in need thereof comprising administering an effective amount of a viral RNA polymerase inhibitor to the subject, wherein said viral infection is a norovirus infection, said inhibitor having the formula

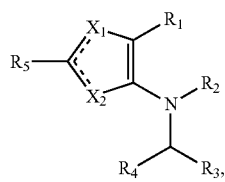

wherein:

$X_1$ and $X_2$ are independently C, NH, O, or S;

$R_1$ is selected from the group consisting of a carboxylic acid, a carboxylate ester, an amide, and an aldehyde group;

$R_2$ is a saturated or unsaturated hydrocarbon selected from the group consisting of straight and branched chain alkyl, which has 1 to about 20 carbons and which may be interrupted with at least one oxygen, nitrogen, or sulfur, alkenyl, alkynyl, cycloalkyl, and aryl;

$R_3$ is a lower alkyl, H, or =O;

$R_4$ is a saturated or unsaturated hydrocarbon selected from the group consisting of straight or branched chain alkyl, which has 1 to about 20 carbons and which may be interrupted with at least one oxygen, nitrogen, or sulfur, alkenyl, alkynyl, cycloakyl, and aryl; and $R_5$ is a saturated or unsaturated hydrocarbon selected from the group consisting of straight and branched chain alkyl, which has 1 to about 20 carbons and which may be interrupted with at least one oxygen, nitrogen, or sulfur, alkenyl, alkynyl, cycloakyl, and aryl or a pharmaceutically acceptable salt thereof.

2. The method of claim 1, wherein said inhibitor is selected from the group consisting of:

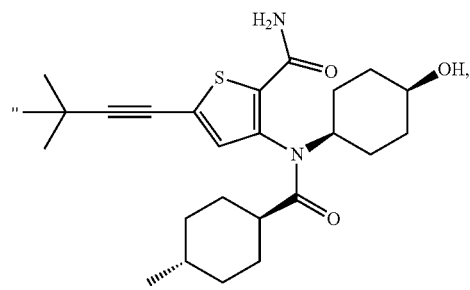

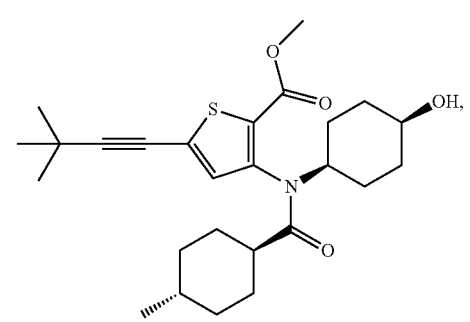

-continued

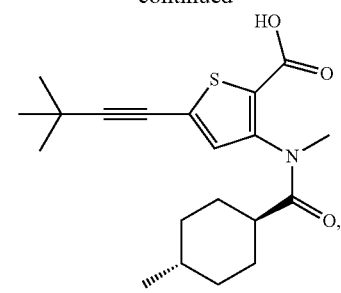

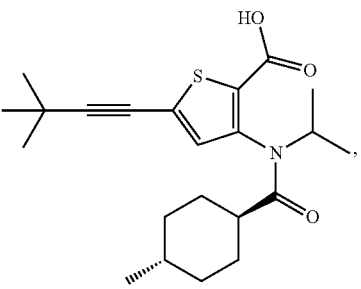

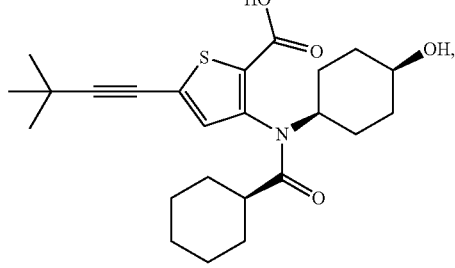

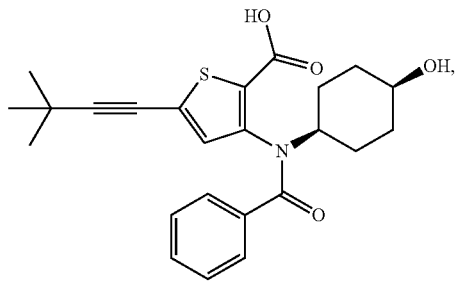

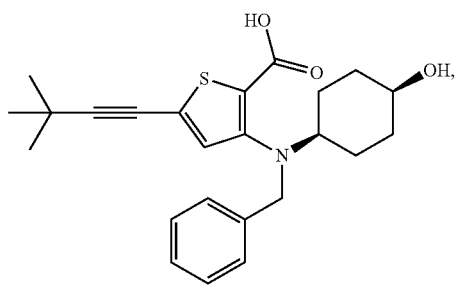

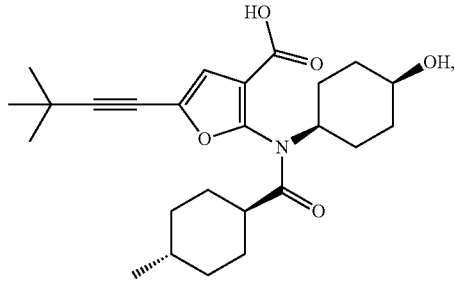

-continued

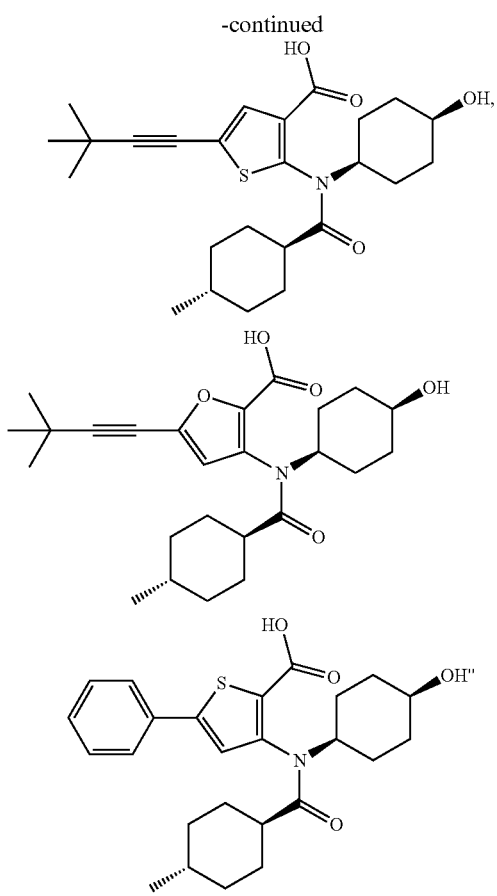

or a pharmaceutically acceptable salt of said inhibitor.

3. A method for treating a viral infection in a subject in need thereof comprising administering an effective amount of a viral RNA polymerase inhibitor to the subject, wherein said viral infection is a norovirus infection, said inhibitor being selected from the group consisting of:

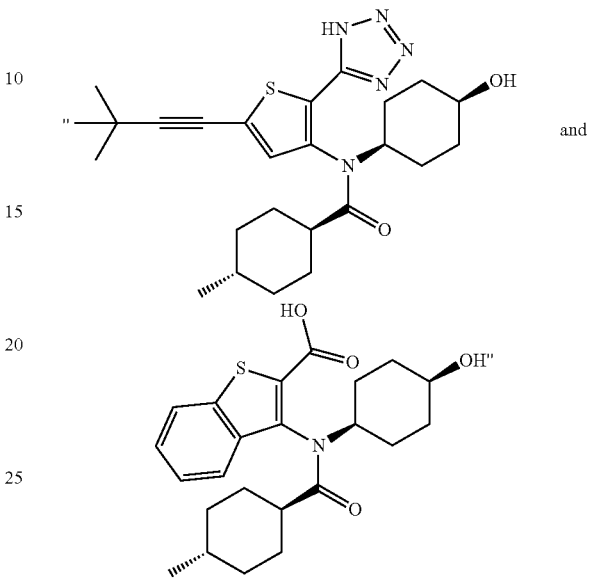

and

4. A method for the treatment of norvirus infection associated with clinical pathology in a patient in need thereof comprising administration of an effective amount of VX-222 or a pharmaceutical salt or prodrug thereof, said VX-222 being effective to inhibit norovirus RNA polymerase activity.

* * * * *